United States Patent
Järvinen

(10) Patent No.: US 6,562,071 B2
(45) Date of Patent: May 13, 2003

(54) FIXATION ANCHOR

(76) Inventor: Teppo Järvinen, Kinnarinkatu 5E, 33530 Tampere (FI)

( * ) Notice: Subject to any disclaimer, the term of this patent is extended or adjusted under 35 U.S.C. 154(b) by 0 days.

(21) Appl. No.: 09/881,563

(22) Filed: Jun. 14, 2001

(65) Prior Publication Data

US 2002/0040241 A1 Apr. 4, 2002

Related U.S. Application Data

(60) Provisional application No. 60/211,501, filed on Jun. 14, 2000.

(51) Int. Cl.$^7$ .................................................. A61F 2/80
(52) U.S. Cl. ........................ 623/13.14; 606/72; 606/232
(58) Field of Search ........................... 623/13.14, 13.11, 623/13.12, 13.13, 13.15, 13.16, 13.17, 13.18; 606/72, 232, 73, 90, 102, 80, 98

(56) References Cited

U.S. PATENT DOCUMENTS

| | | | |
|---|---|---|---|
| 4,870,957 A | | 10/1989 | Goble et al. ............ 128/92 YF |
| 4,955,910 A | | 9/1990 | Bolesky ........................ 623/13 |
| 5,632,748 A | | 5/1997 | Beck, Jr. et al. .............. 606/89 |
| 5,707,395 A | * | 1/1998 | Li ............................... 606/232 |
| 5,725,529 A | | 3/1998 | Nicholson et al. ............ 606/72 |
| 5,931,840 A | | 8/1999 | Goble et al. .................. 606/73 |
| 5,957,953 A | * | 9/1999 | DiPoto et al. ............... 606/232 |
| 6,355,066 B1 | * | 3/2002 | Kim ............................. 606/232 |
| 6,379,361 B1 | * | 4/2002 | Beck et al. .................. 606/104 |

OTHER PUBLICATIONS

Bach, "Arthroscopy–Assisted Patellar Tendon Substitution for Anterior Cruciate Ligament Insufficiency," *Am. J. Knee Surgery*, 2(1):3–20, 1989.

Barber et al., "Preliminary Results of an Absorbable Interference Screw," *Arthroscopic & Related Surgery*, 11(5:537–548, 1995.

Beck et al., "Anterior Cruciate Ligament Reconstruction with the Endoscopic Technique," *Op. Tech. in Orthopaedics*, 12(2:86–98, 1992.

Brand et al., "Graft Fixation in Cruciate Ligament Reconstruction," *Am. J. Sports Med.*, 28(5:761–774, 2000.

Brown et al., "The Use of Hamstring Tendons for Anterior Cruciate Ligament Reconstruction," *Clinics in Sports Med.*, 12(4:723–774, 2000.

Daniel, "Principles of Knee Ligament Surgery," Chapter 2, *Knee Ligaments: Structure, Function, Injury, and Repair*, Raven Press, NY, p. 11–30, 1990.

Fu and Ma, "Anterior Cruciate Ligament Reconstruction Using Quadruple Hamstring," *Operative Techniques in Orthopaedics*, 9(4):264–272, 1999.

Giurea et al., "Comparative Pull–Out and cyclic–Loading Strength Tests of Anchorage of Hamstring Tendon Grafts in Anterior Cruciate Ligament Reconstruction," *Am. J. Sports Med.*, 27(5:621–625, 1999.

(List continued on next page.)

Primary Examiner—Pedro Philogene
(74) Attorney, Agent, or Firm—Banner & Witcoff Ltd.

(57) ABSTRACT

A anchor for fixation of an artificial or natural ligament or tendon into a drill-hole in the bone. The device features an anchoring member and a clamp member. According to one embodiment, the anchoring member is U-shaped with two arms that are joined at one end, around which the transplant is passed. The clamp member is designed to be placed between the two arms of the anchoring member or one arm and the wall of the drill-hole thereby locking the anchor in place in the drill-hole.

64 Claims, 19 Drawing Sheets

OTHER PUBLICATIONS

Havig et al., "Interference Screw Fixation of Soft Tissue ACL Grafts: . . . ," *Proc. Specialty Day, Am. Soc., Orth. Soc. Sports Med.*, p. 28, 1999.

Hoffmann et al., "Initial Fixation Strength of Modified Patellar Tendon Grafts for Anatomic Fixation in Anterior Cruciate Ligament Reconstruction," *J. Arthroscopic & Rel. Surgery*, 15(4):392–399, 1999.

Höhler et al., "Bone tunnel enlargement after anterior cruciate ligament reconstruction: . . . ," *Knee Surg. Sports Traumatol. Arthrosc.*, 6:231–240, 1998.

Ishibashi et al., "The Effect of Anterior Cruciate Ligament Graft Fixation Site at the Tibia on Knee Stability: . . . ," *Arthroscopy*, 13(2):177–182, 1997.

Kurosaka et al., "A biomechanical comparison of different surgical techniques of graft fixation in anterior cruciate ligament reconstruction," *Am. J. Sports Med.*, 15(3):225–229, 1987.

Larson et al., "Fixation Techniques for Hamstring and Other Soft Tissue ACL Grafts," *Proc. Specialty Day, Am. Orth. Soc. Sports Med.*, Orlando, FL, pp. 99–102, 2000.

Matthews et al., "Pitfalls in the Use of Interference Screws for Anterior Cruciate Ligament Reconstruction . . . ," *Arthroscopy*, 5(3):225–226, 1989.

Matthews et al., "Fixation Strengths of Patellar Tendon–Bone Grafts," *Arthroscopy*, 9(1):76–81, 1993.

Pierz et al., "The Effect of Kurosaka Screw Divergence on the Holding Strength of Bone–Tendon–Bone Grafts," *Am. J. Sports Med.*, 23(3):332–335, 1995.

Rupp et al., "Fixation Strength of a Biodegradable Interference Screw and a Press–Fit Technique in Anterior Cruciate Ligament Reconstruction with a BPTB Graft," *Arthroscopy*, 13(1):61–65, 1997.

Safran and Harner, "Technical Considerations of Revision Anterior Cruciate Ligament Surgery," *Clin. Orth. & Rel. Res.*, 323:50–64, 1996.

Schroeder, "Reduction of Femoral Interference Screw Divergence During Endoscopic Anterior Cruciate Ligament Reconstruction," *Arthroscopy*, 15(1):41–48, 1999.

Stähelin and Weiler, "All–Inside Anterior Cruciate Ligament Reconstruction Using Semitendinosus Tendon . . . ," *Arthroscopy*, 13(6):773–779, 1997.

Vainionpää et al., "Surgical Applications of Biodegradable Polymers in Human Tissues," *Prog. Polym. Sci.*, 14:679–716, 1989.

Van der Reis et al., "Comparison of Hamstring Fixation Devices Under Cyclic Loading," *Am. Orth. Soc. Sports Med.*, Orlando, FL, p. 88, 2000.

Weiler et al., "Biodegradable Implants in Sports Medicine," *Arthroscopy*, 16(3):305–321, 2000.

* cited by examiner

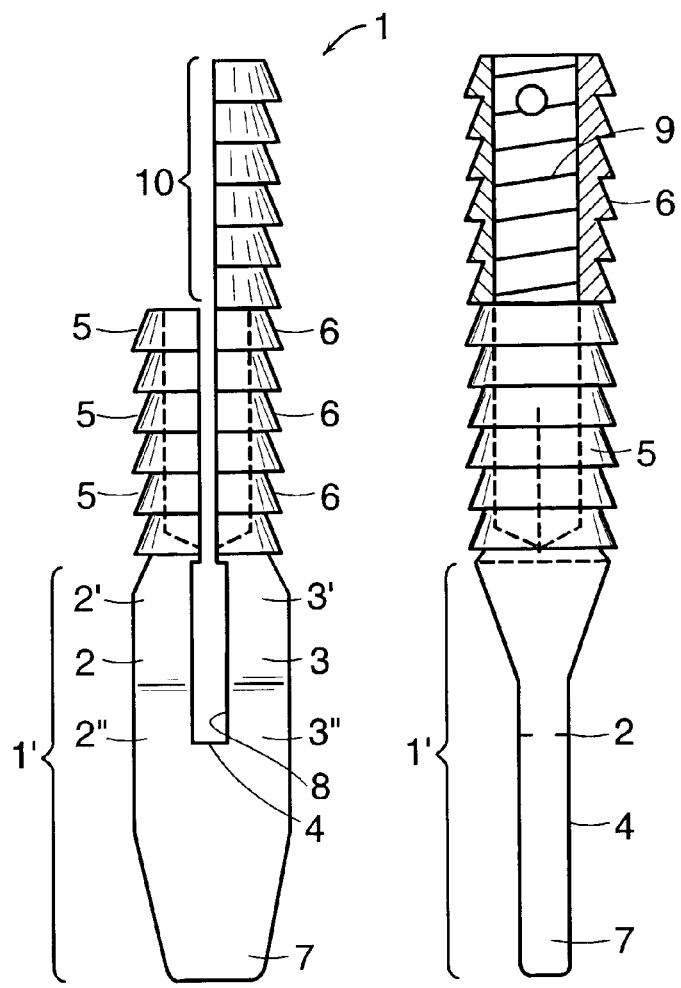
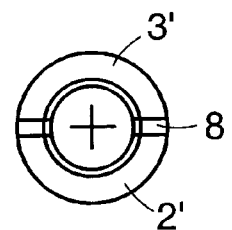
FIG. 2A   FIG. 2B
FIG. 2C

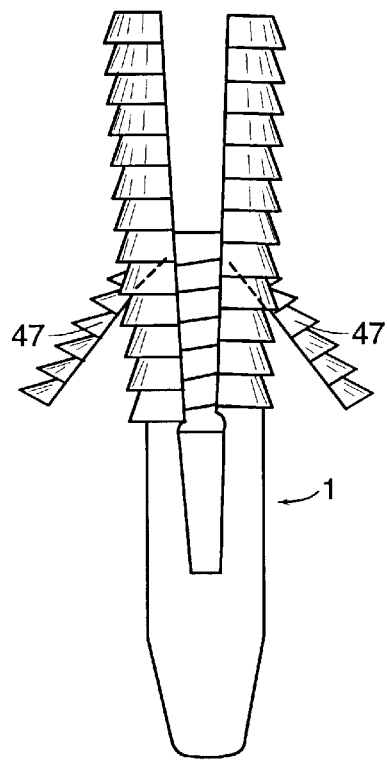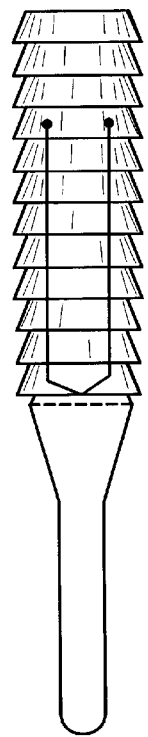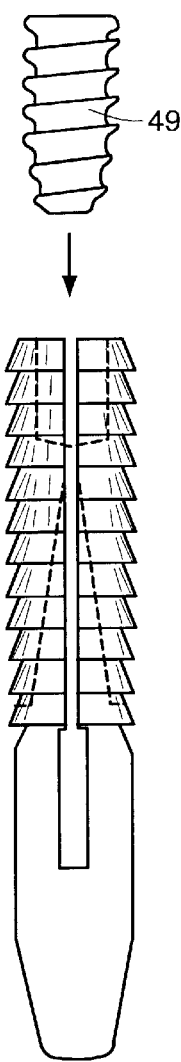
FIG. 13C
FIG. 13A
FIG. 13B

FIXATION ANCHOR

RELATED APPLICATIONS

This application claims the benefit of the filing date of U.S. Provisional Patent Application No. 60/211,501, filed Jun. 14, 2000, hereby incorporated by reference in its entirety.

BACKGROUND OF THE INVENTION

1. Field of the Invention

Embodiments of the present invention are related to orthopaedic surgical devices, such as implants, and procedures using the implants. More particularly, embodiments of the present invention are directed to surgical devices involved in replacing, reconstructing or securing synthetic or biological connective tissue to a bone surface, such as, for example, attaching and maintaining a replacement anterior cruciate ligament (ACL) against a bone.

Embodiments of the present invention particularly relate to surgical implants manufactured of biocompatible (permanent or bioabsorbable) material, e.g., plastic, metal, or bioabsorbable (or biodegradable) polymer, copolymer, polymer alloy or composite and which implants are used for fixation of a synthetic or biological (connective tissue) graft into a drill-hole in a bone. Grafts according to the present invention include natural (auto- or allograft) and/or synthetic substitutes to ligament or tendon. Synthetic implants according to the present invention may be ceramic and/or polymeric and include fibrous braid implants or other implants comprised of fabric.

2. Description of Related Art

Reconstruction is the standard of care after anterior cruciate ligament (ACL) injury. In surgery it is generally known to use an autograft taken e.g., from the knee of the patient, to replace the ruptured ACL. The two most commonly used are the bone-patellar tendon bone (BPTB) and the hamstring tendon (semitendinosus tendon with or without gracilis tendon), although allografts, synthetic grafts and quadriceps tendon grafts have also been used as ACL substitutes. The surgical techniques of the ACL reconstruction using bone-tendon bone (BTB) graft and hamstring tendon graft are described in detail in the following references: Beck, C. L., Jr.; Paulos, L. E.; Rosenberg, T. D.: "Anterior cruciate ligament reconstruction with the endoscopic technique," *Operative Techniques in Orthopaedics*, 2:96–98, 1992; Stähelin, A. C.; Weiler, A.: "All-inside anterior cruciate ligament reconstruction using semitendinosus tendon and soft threaded biodegradable interference screw fixation," *Arthroscopy*, 13:773–779, 1997; Fu, F. H.; Ma, C. B.: Anterior Cruciate Ligament Reconstruction Using Quadruple Hamstring. *Operative Techniques in Orthopaedics*, 9:264–272, 1999. Additional references of interest include Hoffman, R. F. G.; Peine, R; Bail, H. J.; Sudkamp, N. P.; Weiler, A.: "Initial fixation strength of modified patellar tendon grafts for anatomic fixation in anterior cruciate ligament reconstruction," *Arthroscopy*, 15:392–399, 1999.

In brief, the ruptured ACL is removed and drill-holes are made into the distal femur and proximal tibia into or into close vicinity of the original insertion sites of the ACL. The replacement substitute (graft) is harvested either from the patellar tendon (BTB) or from the semitendinosus- and gracilis muscle tendons (hamstring graft), pulled through the drill-holes to replace the ruptured ACL and finally fixed into these drill-holes, leaving the tendon part to act as a new ACL.

Rigid fixation of the ACL graft has been recognized as one of the most important factors that determine the long-term success of an ACL reconstruction (Kurosaka, M; Yoshiya, S; Andrish, J T: "A biomechanical comparison of techniques of graft fixation in anterior cruciate ligament reconstruction, *Am. J. Sports Med.*, 15:225–229, 1987; Brand, J., Weiler, A., Caborn, D. N. M., Brown, C. H. Johnson, D. L.: "Current Concepts: Graft Fixation in Cruciate Ligament Reconstruction." *Am. J. Sports Med.* 28: 761–774, 2000). Further, the tibial fixation of hamstring tendon grafts is considered more problematic than femoral fixation (Larson, R.: "Fixation techniques for hamstring and other soft tissue ACL grafts. The science: Comparative laboratory and clinical studies," *Proceedings of the Specialty Day*, the American Orthopaedic Society for Sports Medicine p. 99–102, Orlando, Fla., Mar. 18, 2000; Brand, J., Weiler, A., Caborn, D. N. M., Brown, C. H. Johnson, D. L.: "Current Concepts: Graft Fixation in Cruciate Ligament Reconstruction." *Am. J. Sports Med.* 28: 761–774, 2000), mainly because the forces are subjected to the ACL substitute (graft) parallel with the tibial bone tunnel and the bone quality is substantially inferior in the tibia than in the femur.

Among the currently available soft tissue (hamstring) graft fixation implants, interference technique, in which the so called interference screw is inserted into the space between the drill-hole and the end of the graft to lock the graft into the drill-hole, is currently the most commonly used method to secure an ACL substitute to a bony drill-hole in an ACL reconstruction. The fixation screws, like interference screws, are normally made of metal, like stainless steel or titanium or of a bioabsorbable polymer, like polylactide. Metallic and/or bioabsorbable polymeric materials and composites suitable for manufacturing of fixation screws, are described in the literature (Vainionpää, S.; Rokkanen, P.; Törmälä, P.: "Surgical Applications of Biodegradable Polymers in Human Tissues." *Progr. Polym. Sci.*, 14:679–716, 1989; Weiler, A.; Hoffman, R. F. G.; Stahelin, A. C.; Helling, H. J.; Sudkamp, N. P.: Biodegradable Implants in Sports Medicine: The Biological Base. Current Concepts *Arthroscopy* 16:305–321, 2000).

During interference screw insertion, technical complications such as the threads of the screw damaging the graft or passing sutures, the graft rotating with the screw so that the optimal position of the graft is lost and/or the graft is damaged or the screw becomes inserted non parallel (divergent) to the graft thereby significantly decreasing the strength of fixation, often occur. There are also concerns specific to the metal interference screws. For example, in case of a need for revision surgery, metal screws can significantly complicate the operation, as the hardware inserted in the primary reconstruction has to be removed, sometimes resulting in considerable loss of bone in the fixation site, and thus, decreasing the strength of the fixation of the revised graft. In most severe cases, it may even be necessary to perform bone grafting prior to revision surgery (Brown, C. H.; Steiner, M. E.; Carson, E. W.: "The uses of hamstring tendons for anterior cruciate ligament reconstruction: Technique and results," *Clin. Sports Med.*, 12:723–756, 1993; Schroeder, F. J.: "Reduction of femoral interference screw divergence during endoscopic anterior cruciate ligament reconstruction," *Arthroscopy*, 15:41–48, 1999). Metal screws have also been shown to disturb postoperative MRI evaluation (Shellock, F. G.; Mink, J. H.; Curtin, S.; Friedman, M. J.: "MR imaging and metallic implants for anterior cruciate ligament reconstruction: assessment of ferromagnetism and artifact," *J. Magn. Reson. Imaging*, 2:225–228, 1992). The problems specific to metal screws can naturally be avoided by the use of screws made of bioabsorbable materials, but other problems arise, such as the bioabsorbable screw breaking during screw insertion. Also, the drill-hole has to be threaded for the insertion of the bioabsorbable screw, which not only delays surgical operation, but also increases trauma and removes mechanically stronger cortical bone, thus reducing the grip of the screw into the bone. Complications associated with the surgical technique, like those listed above, are also provided in the literature (Bach, B. R.: "Arthroscopy-assisted patellar tendon substitution for anterior cruciate ligament insufficiency," *Am. J. Knee Surg.*, 2:3–20, 1989; Barber, A. F.; Buxton, E. F.; McGuire, D. A.; Paulos, L. E.: "Preliminary results of an absorbable interference screw," *Arthroscopy*, 11:537–548, 1995; Matthews, L. S.; Soffer, S. R.: "Pitfalls in the use of interference screws for anterior cruciate ligament reconstruction: Brief report," *Arthroscopy*, 5:225–226, 1989; Matthews, L. S.; Lawrence, S. J.; Yahilo, M. A.; Sinclair, M. R.: "Fixation strength of patellar tendon-bone grafts," *Arthroscopy*, 9:76–81, 1993; Pierz, K.; Baltz, M.; Fulkerson, J.: "The effect of Kurosaka screw divergence on the holding strength of bone-tendon-bone grafts," *Am. J. Sports Med.*, 23:332–335, 1995; Rupp, S.; Krauss, P. W.; Fritsch, E. W.: "Fixation strength of a biodegradable interference screw and a press-fit technique in anterior cruciate ligament reconstruction with a BPTB graft," *Arthroscopy*, 13:61–65, 1997; Safran, M. R.; Harner, C. D.: "Technical considerations of revision anterior cruciate ligament surgery," *Clin. Orthop.*, 323:50–64, 1996).

Finally, although providing a possibility for a bioabsorbable and apertural (anatomic) fixation of the ACL substitutes and despite their adequate initial fixation strength in pull-out studies, interference technique has been shown to result in early slippage or even complete failure of the graft-anchor-bone complex during cyclic loading of hamstring grafts fixed interference screws (Giurea, M., Zorilla, P. Amis, A. A., Aichroth, P.: "Comparative Pull-Out and Cylic-Loading Strength Tests of Anchorage of Hamstring Tendon Grafts in Anterior Cruciate Ligament Reconstruction." *Am. J. Sports Med.* 27: 621–25, 1999; Havig, M. T.; Paulos, L. E.; Weiss, J.; Ellis, B. S.; Bote, H.: "Interference screw fixation of soft tissue ACL grafts: Effects of cyclic loading on initial fixation strength," *Proceedings of the Specialty Day, the American Orthopaedic Society for Sports Medicine*, p. 28, Anaheim, Calif. Feb. 7, 1999; Van der Reis, W. L.; Deffner, K. T.; Rosenberg, T. D.: "Comparison of hamstring fixation devices under cyclic loading," *Proceedings of the Specialty Day*, the American Orthopaedic Society for Sports Medicine, p. 88, Orlando, Fla., Mar. 18, 2000; Brand, J., Weiler, A., Caborn, D. N. M., Brown, C. H. Johnson, D. L.: "Current Concepts: Graft Fixation in Cruciate Ligament Reconstruction." *Am. J. Sports Med.* 28: 761–774, 2000).

Because of complications found in clinical use of interference screws, several attempts have been done to develop other types of anchoring devices for fixation of synthetic or natural ligaments or tendons in ACL reconstruction. For example, free tendon grafts can be fixed outside the drill-holes using either staples, screws and washers, so-called endobuttons, or tying sutures over buttons or screw posts.

Extra-articular or suspensory fixation methods, for example, methods that require fixation outside the bone tunnel such as is found with staples placed either on the anterior cortex of the tibia or implants with staples placed partially within an entrance opening of the tunnel, are another commonly used alternative to fix soft tissue grafts into bone drill-holes. Although these methods have been shown to provide superior fixation strengths to the interference technique, they require at least that a portion of the implant be exterior to the drill-hole. Further, in comparison to the apertural fixation methods, the stiffness of the suspensory methods has been shown to be clearly inferior (Ishibashi, Y; Rudy, T. W.; Livesay, G. A.; Stone, J. D.; Fu, F. H.; Woo, S. L.: "The effect of anterior cruciate ligament graft fixation site at the tibia on knee stability: Evaluation using a robotic testing system," *Arthroscopy*, 13:177–182, 1997). Suspensory or extra-articular fixation of grafts has also been accused of permitting micromotion of the individual tendons of the four-strand graft within the bone tunnel, which in turn, has been associated with the enlargement of the bone tunnels, increased AP-laxity and decreased stiffness of the reconstruction, possibly jeopardizing the success of the operation (Hoher, J., Moller, H. D., Fu, F. H. "Bone Tunnel Enlargement after Interior Cruciate Ligament Reconstruction: Fact or Fiction?" *Knee Surg. Sports Traumatol. Arthrosc.* 6:231–240, 1998).

Crossbar or toggle fixators are the latest in the fixation implants developed to secure tendon graft in bone tunnel. In short, the basic principle of these implants is that the tendon(s) is/are looped over a crossbar/toggle-like structure placed in the bone drill-hole. To date, these devices have been designed for the femoral fixation of hamstring grafts, with two exceptions:

UK Pat Appl. GB 2 288 739 describes an anchor for anchoring a ligament or the like at or adjacent one end of a bone or channel in a bone, comprising a head portion and a near portion adapted to extend into the bone or channel and to receive the ligament. Even if this implant can be applied for fixation (anchoring) a ligament, it has the head portion which remains outside of the drill-hole on the surface of bone. This portion, located on bone surface, causes tension in soft-tissue on bone. This tension can cause irritation, pain and foreign body reactions (swelling or oedema) in soft tissue. The head portion may also be palpable below the skin, which is inconvenient for the patient. Further, this implant does not provide an anatomic fixation or enable the tensioning of the graft.

A more advanced version of the same principle has been described in GB 2,337,463, which is otherwise very similar to the device described in GB 2,288,739 except of having the means for holding the ligament under tension, and then, when appropriate tension is achieved, maintaining the desired tension by a locking means comprising of a crimpable washer and a lock nut. Although enabling the tensioning of the graft, this design is also not endosteal (intraboreal) and does not provide an anatomic fixation.

U.S. Pat. No. 5,632,748 describes an endosteal anchoring device for urging a ligament graft against a bone surface comprising an anchoring body, a member for resisting slippage of the anchoring body into the periphery of a bone tunnel under ligament tension, a member for avoiding puncturing, piercing or tearing of cross-fibers of the ligament graft and a member for urging the ligament graft flush against the inner surface of the bone tunnel for accelerated healing. This device can be located totally inside of the drill-hole of bone. However, this device is bulky because (a) the anchor member, (b) the ligament graft, which is encircled around the anchor member and positioned within the cross-sectional area of the groove on the anchor member and (c) the insertion member (which in combination with the anchor member provides a means of locking the ligament graft at a fixation site) all are located side by side inside of the drill-hole. Therefore a substantial amount of the drill-hole is filled with the device (anchor member+insertion member) and typically less than half of the space inside of drill-hole is left for the ligament graft, as can be seen from FIG. 1, FIG. 3, FIG. 6, FIG. 8 or FIG. 9 of U.S. Pat. No. 5,632,748. When the device is bulky in comparison to the ligament it means that a large amount of degradable foreign material is located near the ligament. Accordingly, the diameter of the drill-hole must be substantially larger than the diameter of the ligament. Also a large amount of foreign material means a large amount of polymer debris degrading in the vicinity of the ligament, resulting in an increasing risk for compromised healing of the ligament.

FI. Pat. No. 100217 B describes an implant for fixation of a tendon loop in ACL reconstruction. The implant comprises the first end which includes a hole through which a tendon has been slipped to form a loop and a transverse locking element for locking of the implant into the drill-hole inside of bone. The implant further comprises a base member which includes a fixation notch for inserting an installation instrument. Even if this fixation implant will be located totally inside of the drill-hole into the bone, the installation of the transverse locking element is difficult and causes the formation of additional trauma (wound into the soft tissues and an additional transverse hole into the bone)

U.S. Pat. No. 5,425,767 describes an anchor for an artificial ligament in a bone. The anchor comprises a Y-shaped socket having first and second arms angled with respect to each other. The first arm is sized to receive the ligament and has cross-grooves for gripping the ligament. A bullet shaped clamp element is rotatably mounted to the second arm. The clamp element also has grooves that directly contact the ligament to apply an oblique force against the ligament. The clamp element and cross-grooves in the first arm completely surround and compress the ligament to frictionally secure the ligament to the socket. This implant is bulky, because of the intersecting openings (the Y-shape) of the socket. Therefore the opening of the drill-hole in the bone must be significantly larger than the drill-hole deeper inside of bone. A larger drill-hole opening means increased trauma to the bone surface. Additionally the clamp element compresses the ligament, which may cause similar problems for the ligament as found with the fixation of a ligament with an interference screw.

U.S. Pat. No. 5,899,938 describes a graft ligament anchor comprising a graft ligament engagement member disposed in an opening in a bone, the graft ligament engagement member being arranged to receive a graft ligament alongside the engagement member, and a locking member for disposition in the opening, and at least in part engageable with the graft ligament engagement member. Movement of the locking member in the opening causes the locking member to urge the engagement member, and the graft ligament therewith, toward a wall of the opening to secure the graft ligament to the wall of the opening. Also in this case the compressing of the ligament may cause problems by damaging the ligament and/or by disturbing its nutrition and healing.

As illustrated by the foregoing summary, efforts are continuously being made to improve devices, instruments and surgical methods used in replacing and reconstructing torn or dislocated ligaments so as to make the process more efficient and effective. However, significant disadvantages still remain with all the presently known devices and methods offered by the prior art.

Accordingly it would be advantageous to overcome the disadvantages of the prior art and to design an implant for use in securing a transplant, such as a hamstring tendon graft, in a bone, such as a tibia, that would: (a) be bioabsorbable; (b) provide a rigid fixation of the transplant at the tunnel opening (apertural/anatomic fixation); (c) have no external hardware, i.e. the implant should be a completely intraboreal or endosteal design such that no part of the implant should protrude outside the bone drill-hole or be located on the outer surface of the tibia; (d) require no additional surgical trauma in addition to the single drill-hole in the tibia as would occur with additional drill-holes or additional skin incisions, etc.; (e) permit/provide a circumferential contact, i.e. ideally 360° contact, between the transplant and bone drill-hole walls, and (f) enable tensioning of the transplant before it is secured into the drill-hole, e.g., by pulling the transplant/implant construct by hand.

SUMMARY OF THE INVENTION

Embodiments of the present invention are directed to implants that can be used to secure a graft or transplant, such as a tendon, to bone, and more particularly, within a hole that is drilled into bone, i.e. a so-called "drill-hole". Drill-holes, according to the present invention, can be made into or through a bone. When the drill-hole is made through a bone, it has an entrance opening and a corresponding exit opening. In addition to its ordinary and accustomed meaning, the term "transplant" includes according to specific embodiments an artificial or natural ligament or tendon graft that is used as a reconstruction material to replace a torn/injured ligament, e.g. an anterior cruciate ligament. The implants of the present invention may also be referred to herein as "anchors" as they anchor or secure the transplant to the bone. The anchors are designed to be placed completely within a drill-hole with no part of the anchor protruding beyond the surface of the bone adjacent to the opening of the drill-hole once it has been properly implanted. Stated differently, the anchor is absent from the surface of the bone after the implantation surgery.

The anchor of the present invention includes an anchoring member and a clamp member. The anchoring member includes an anchor element and a locking element connected to the anchor element, preferably in series relation. The anchor element is configured to retain the transplant such as by allowing the transplant to loop around the anchor element. According a certain embodiment of the invention, the anchor element may include a groove, hole or other opening through which the transplant may be slid or inserted and then looped around the anchor element. However, the anchor element may include a wide variety of other configurations to retain a transplant such as the anchor element being uni- or multi-compartmental and including a slot, a hole, a hook, one or more tabs or extensions or other types of a recess through or around which a transplant can be looped.

The portion of the anchor element forming the groove, hole or other opening has a surface area and is configured so as to allow the transplant to be looped without any substantial compression, crimping, cutting or other deleterious effect on the transplant. According to a certain embodiment, the surface area is smooth and free from structure which would abrade or otherwise damage the transplant. The transplant, when looped, is co-extensive with a portion of the length of the anchor element. The anchor element around which the transplant is looped advantageously serves to encourage contact between the wall of the drill-hole and the transplant, and in particular, at the intra-articular opening of the drill-hole, to facilitate healing and securing of the transplant to the bone. The anchor element around which the transplant is looped is configured so as to exclude excessive compression of the transplant against the wall of the drill-hole.

However, the transplant, when looped, is advantageously non-extending along the entire length of the anchoring member. That is, according to the present invention, the anchoring member is configured such that the transplant need not extend along the entire length of the anchoring member, but rather can be fixedly retained within a drill-hole by being looped around only a portion of the anchoring member, such as the anchor element, with the remaining portion of the anchoring member, such as the locking element, being free of transplant contact.

The locking element extends as one or more arms from the anchor element and, in certain embodiments of the invention, includes frictional elements that frictionally engage a wall of the drill-hole. Thus, the locking element serves to prevent the anchoring member from slipping out of the drill-hole. A clamp member is provided which engages the anchoring member to provide further frictional force between the anchoring member and the wall of the drill-hole and to further secure or "lock" the anchoring member within the drill-hole. The clamp member is designed to engage the anchoring member within the drill-hole with no part of the clamp member protruding beyond the surface of the bone adjacent to the opening of the drill-hole. Stated differently, the clamp member, when fully engaged with the anchoring member once proper fixation has been achieved, is absent from the surface of the bone.

According to certain embodiments of the present invention, the locking element is generally cylindrical in design and has a width or diameter that is equal to or slightly less than the diameter of the drill-hole so as to provide for a snug fit of the anchoring member into the drill-hole while still facilitating ease of adjusting the anchoring member within the drill-hole. Although it can be, the diameter of the drill-hole need not be any larger than the width or diameter of the locking element because the transplant does not contact the locking element at a position where the locking element contacts the wall of the drill-hole. Also, the locking element itself may be fashioned from compressible materials allowing its insertion into a drill-hole having substantially the same diameter as the locking element.

According to certain embodiments of the present invention, the locking elements are free from transplant contact. The transplant is not present between the wall of the drill-hole and the locking elements, i.e. the locking elements make direct contact with the wall of the drill-hole. Since the transplant is coextensive with only a portion of the anchoring member, such as the anchor element, any contact between the transplant and degraded material from the anchoring member is advantageously minimized.

In view of the foregoing, it is an object of the present invention to provide an ACL reconstruction fixation implant or anchor for fixation of tendon or synthetic grafts inside of a drill-hole. The implant is safe and simple to insert into a drill-hole with minimal trauma.

Another object of the present invention is to provide a device which is manufactured of biocompatible (permanent or bioabsorbable) material, e.g., plastic, metal, or bioabsorbable (or biodegradable) polymer, copolymer, polymer alloy or fiber reinforced or particle filled bioabsorbable polymer composite, which implant could be inserted into a drill-hole made into a bone, to fixate an ACL graft into the drill-hole.

It is also an object of the present invention to provide an ACL reconstruction fixation device which has such a geometry that the implant slips easily into the drill-hole but expresses, when locked into the drill-hole, a strong resistance against slip-in or pull-out from the drill-hole.

It is another object of the present invention to provide a device for fixing an ACL graft into a bone, which does not interfere with non-invasive examinations (such as radiographs, MRI or CT), is biocompatible and results in/provides a strong and rigid fixation of a graft in ACL reconstruction.

Further, it is an object of the present invention to provide an ACL reconstruction fixation device that does not damage the graft and minimally disturbs the tissue metabolism and blood circulation, when located totally inside of a drill-hole in a bone so that no part of the implant protrudes the outer surface of the bone.

It is a still further object of the present invention to provide an ACL reconstruction fixation device which locks the tendon loop effectively inside of the drill-hole with minimal contact between the tendon and the device, thus enabling maximal filling of the drill-hole with the tendon substance and facilitating effective growth of tendon tissue to contact with the walls of the drill-hole.

It is also a still further object of the present invention to provide an ACL reconstruction fixation device which presses the individual (tendon) bundles of the graft firmly against the walls of the drill-hole at or near the intra-articular tunnel opening (apertural/anatomic fixation).

Consistent with the foregoing objects, and in accordance with the invention as embodied and broadly described herein, a permanent or bioabsorbable intraboreal (endosteal) graft fixation anchor for being simply and safely inserted into a hole or drill canal made into a bone, to securely fix a tendon graft (transplant) into the drill-hole, the anchor device comprising an anchoring member and a clamp member, the anchoring member including an anchor element for holding a loop of a transplant and a locking element to engage a clamp member in a manner to secure or lock the anchor within a drill-hole. The anchor device provides for the rigid fixation of the transplant against the walls of the drill-hole at or near the intra-articular tunnel opening to facilitate the healing of the transplant.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of accompanying drawings in which:

FIG. 2A shows, as a side view, the anchoring member of one embodiment of the invention.

FIG. 2B shows, as a side view, the anchoring member of FIG. 2A, when turned 90 degrees clockwise around its long (vertical) axis.

FIG. 2C shows the anchoring member of FIGS. 2A–2B when seen from above.

FIG. 13A shows, as a side view, the anchoring member of one embodiment of the invention having recesses which expand out in response to a clamp member engaging the anchoring member.

FIG. 13B shows, as a side view, the anchoring member of FIG. 13A, when turned 90 degrees clockwise around its long (vertical) axis and a clamp member to be inserted to lock the anchoring member into the drill-hole in the bone.

FIG. 13C shows how the recesses of the anchoring member are brought out by the insertion of the clamp member to securely fix the anchor into the drill-hole in bone.

Those skilled in the art will recognize that the embodiments depicted in FIGS. 1–15 are not necessarily to scale. Certain dimensions, such as the longitudinal dimensions of the anchor, may have been enlarged, relative to the dimensions of the bone. One skilled in the art, given the benefit of this disclosure, will be able to design and manufacture anchors having widths, lengths, dimensions, and geometries suitable for an intended use.

DETAILED DESCRIPTION OF CERTAIN PREFERRED EMBODIMENTS

It will be readily understood that the components of the present invention, as generally described and illustrated in the Figures herein, could be arranged and designed in a wide variety of different configurations. Thus, the following more detailed description of the preferred embodiments of the endosteal graft fixation anchor and method of the present invention, as presented in FIGS. 1 through 15, is not intended to limit the scope of the invention, as claimed, but it is merely representative of the presently preferred embodiments of the invention.

Figures 1A, 1B:
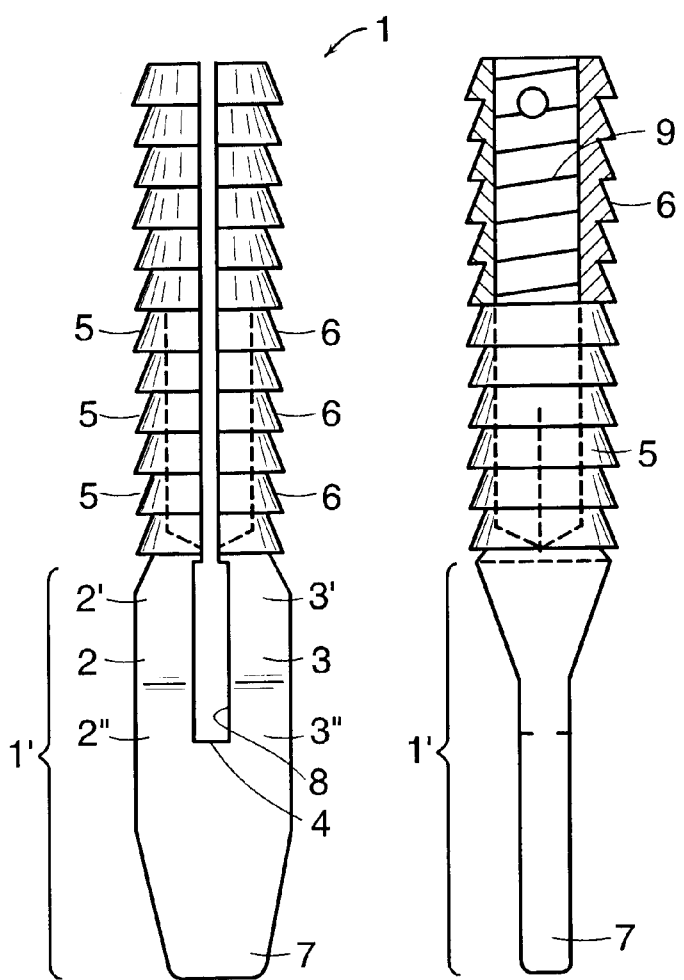
FIG. 1A shows, as a side view, the anchoring member of one embodiment of the invention.
FIG. 1B shows, as a side view, the anchoring member of FIG. 1A, when turned 90 degrees clockwise around its long (vertical) axis.
Figure 1C:
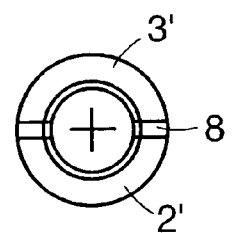
FIG. 1C shows the anchoring member of FIGS. 1A–1B when seen from above.

FIGS. 1A through 1C illustrate one embodiment of an anchoring member 1 of the fixation implant in accordance with the invention. FIG. 1A is a side view of an embodiment of the anchoring member 1. FIG. 1B is a side view when the anchoring member 1 of FIG. 1A has been turned 90 degrees clockwise around its long axis. FIG. 1C is a view from upper direction along the long axis of the anchoring member 1. In general, anchoring member 1 includes an anchor element shown generally at 1' and a locking element which is shown in FIG. 1 as arms 2 and 3 extending integrally and in series relation from anchor element 1'.

Specifically, the anchoring member 1 of the implant of the present invention comprises a U-shaped anchor body or anchor element 1' for placement into a drill-hole in a bone, from the anchor body or anchor element 1' emerging two arms 2 and 3 with first ends 2' and 3' and second ends 2" and 3" which join at the connecting portion 4, around which the ligament(s) passes. As can be seen in FIG. 1A, arms 2 and 3 include a plurality of locking protrusions shown at 5 and 6. The locking protrusions 5 and 6 are typically protuberances emerging from the surface of the implant. Such protuberances are e.g., threads, barbs, pyramids or transverse ridges. The geometry of protrusions is such that the anchoring member 1 slips easily into the drill-hole in a bone but does not move at all once it has been locked into the drill-hole. According to the advantageous embodiments of FIGS. 1A–B, the locking protrusions 5 and 6 are transverse ridges emerging from the surface of the implant. Also other geometries of the locking protrusions, like barbs or threads, are possible in implants of the invention. In addition, the arms can be wholly or partially covered with the locking protrusions.

The connecting part 4 of the anchor element can include an extension part 7 which urges said ligament(s) against a bone surface within the drill-hole. The two arms 2 and 3 and the connecting portion 4 (with an optional extension part 7) form a slot 8 into which the ligament(s) can be threaded or slipped. As can be seen in FIGS. 1A–C, the locking element formed by the two arms is substantially cylindrical in design so as to contour to a standard drill-hole. In this manner the anchoring member achieves substantial contact with the wall of the drill-hole so as to maximize the ability of the anchoring member to retain itself within the drill-hole. As can be further seen in FIGS. 1A–C, the anchor element tapers from the locking element to form a generally rectangular tab. The tip portion of the tab indicated at 7 is angled to promote guidance and ease of insertion into a drill-hole. Anchoring member 1 is generally flexible such that the two arms 2 and 3 may be pulled apart to enlarge the groove 8 for insertion of a graft. The two arms then retract into their original position. As can be seen in FIG. 1B, the interior of the locking element has threads 9 to receive a correspondingly threaded clamp member (not shown).

FIGS. 2A through 2C illustrates the anchoring member 1 of another embodiment of the invention. FIG. 2A is a side view of an embodiment of an anchoring member 1. FIG. 2B is a side view when the anchoring member 1 of FIG. 2A has been turned 90 degrees clockwise around its long axis. FIG. 2C is a view from upper direction along the long axis of the anchoring member 1. According to FIGS. 2A and 2B one of the first ends of the arms, here 2', has been shortened, and the other, here 3', includes elongated gripping element 10. Elongated gripping element 10 is used to insert and/or remove the anchoring member into or out of the drill-hole. Although elongated gripping element 10 is shown as the portion of the arm 3 that extends beyond arm 2, the elongated gripping element 10 can be a separately extending tab and may or may not include locking protrusions.

Figure 3A:
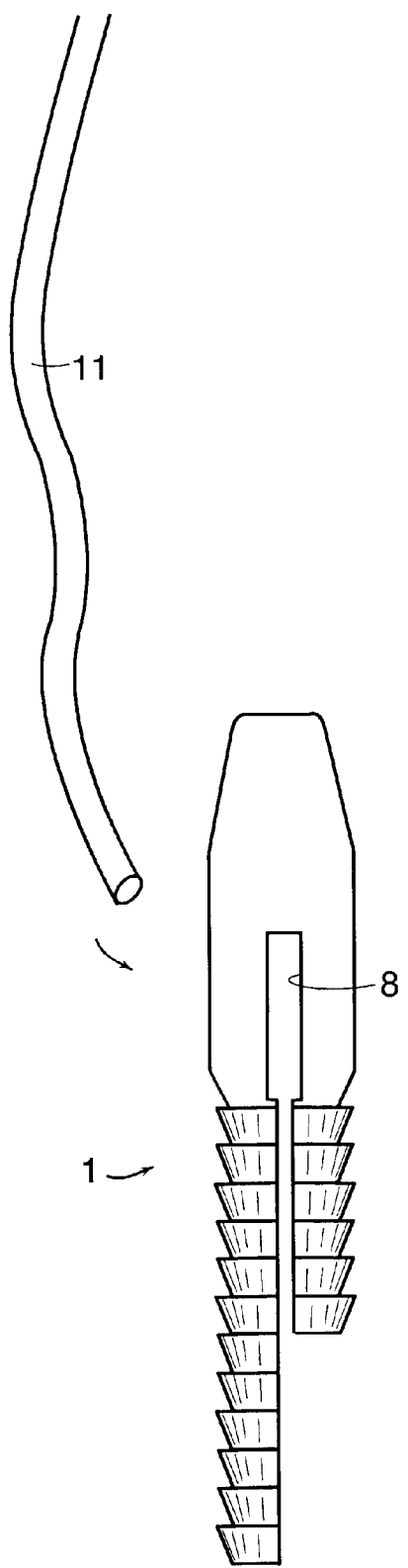
FIG. 3A shows, as a side view, the anchoring member of one embodiment of the invention and a tendon graft.
Figure 3B:
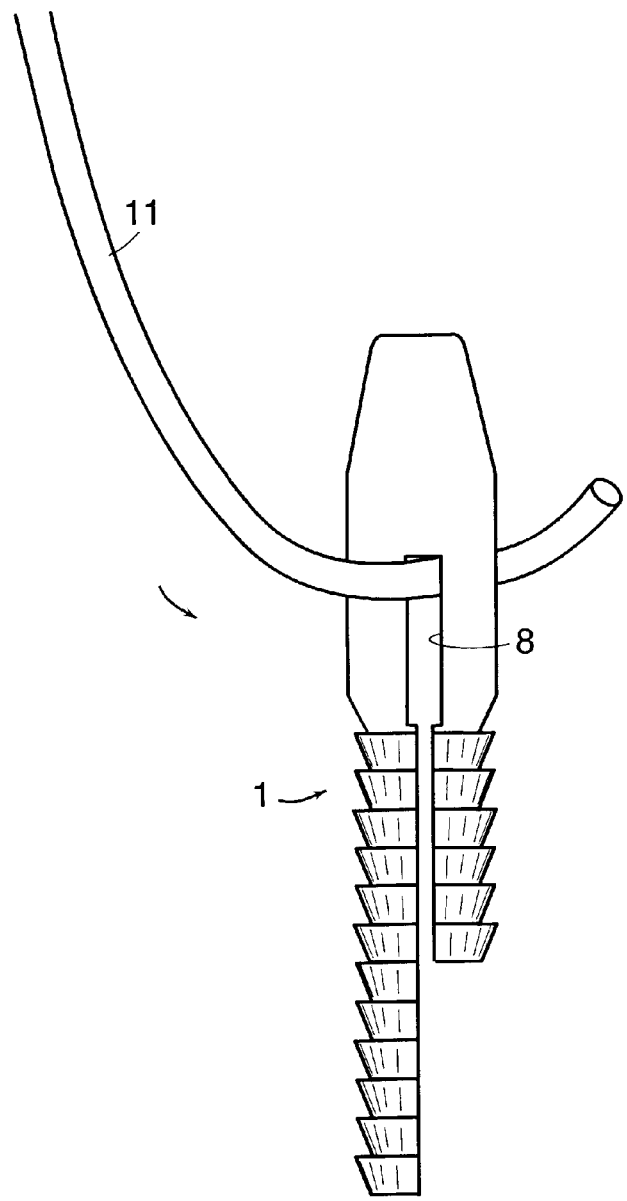
FIG. 3B shows, as a side view, how the tendon graft can be threaded into the slot or opening in the anchoring member of FIG. 3A.

FIGS. 3A and 3B show how a transplant, such as a ligament or tendon graft 11, can be threaded into the slot 8 in the anchoring member 1. According to the present invention, a transplant, such as a tendon, is generally of a strand configuration. The tendon 11 is then simply inserted into and out of the opening or groove 8 and then looped around the anchor element away from the locking element. In this manner, the tendon is coextensive with a portion of the anchor element and on opposite sides of the anchor element.

Figures 4A, 4B, 4C:
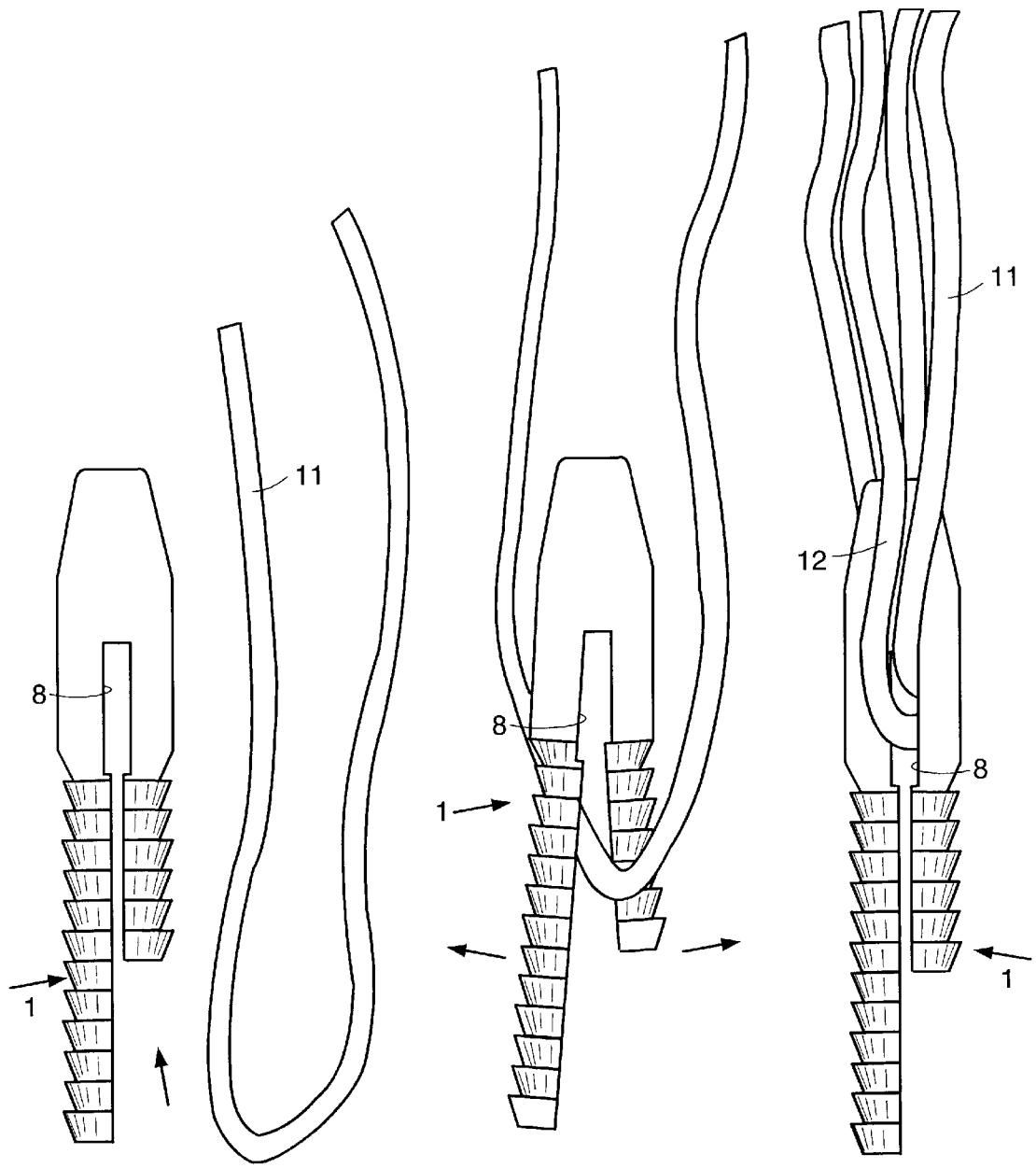
FIG. 4A shows, as a side view, the anchoring member of the invention and a tendon graft.
FIG. 4B shows, as a side view, how the tendon graft can be slid into the slot or opening in the anchoring member of FIG. 4A.
FIG. 4C shows, as a side view, how another loop of the tendon graft (or another tendon graft) can be slid into the slot or opening in the anchoring member of FIG. 4A and the two tendons can be bent parallel with each other.

FIGS. 4A–4C show how two transplants, such as a two-strand tendon (or two loops of the same tendon) 11 and 12 can be slid into the slot 8 in the anchoring member 1. According to the present invention, the two arms of the locking element are pulled apart slightly to enlarge the space between them and, accordingly, the groove 8 as well, as depicted by the arrows in FIG. 4B. The tendon 11 is then slid between the two arms of the locking element and into the groove 8.

FIG. 4C shows, as a side view, how both ends of the two tendon grafts 11 and 12, which are threaded into the slot 8 in the anchoring member 1, can be bent or positioned parallel with each other. The parallel ends of the tendons can then be joined together e.g., by the suturing and thereafter this sutured end of the tendon transplant can be fixed into a drill-hole in a bone e.g., with an interference screw as is described e.g., in FIG. 5.

Figure 5:
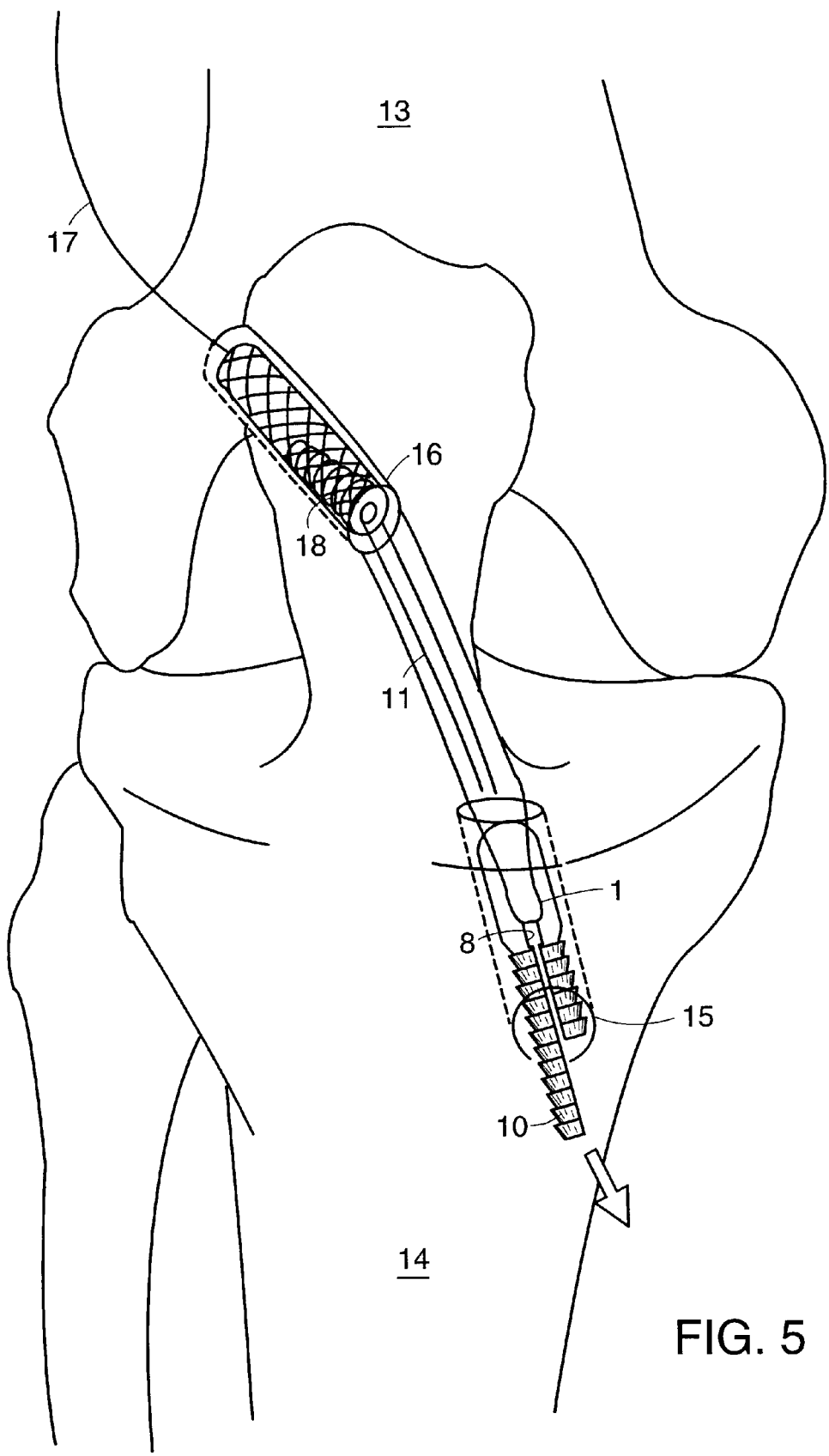
FIG. 5 is a diagrammatical view of a human knee joint illustrating the tightening of an anterior cruciate ligament transplant between femur and tibia with the anchoring member of the invention, which is described in FIGS. 1–4.

FIG. 5 is a diagrammatical view of a human knee joint illustrating the tightening of an ACL transplant (tendon or ligament) 11 between femur 13 and tibia 14 with the anchoring member 1 of the invention. As can be seen in FIG. 5, a drill-hole 15 is formed in tibia 14 which has an entrance opening and an exit opening. A drill-hole having an entrance opening and an exit opening is also formed in femur 13. The transplant 11 has been threaded through the slot 8 of the anchoring member 1 to form a loop (according to FIGS. 3B–C) and the two free (not looped) ends of the transplant (graft) have been sutured together. This sutured end of the transplant 11 has then been drawn through a drill-hole 15 in tibia and into a drill-hole 16 in femur, e.g., with a passing suture 17. After drawing the transplant 11 with the passing suture 17 through the tibial drill-hole 15 into the femoral drill-hole 16, the transplant 11 has been fixed into the femoral drill-hole 16 with an interference screw 18. The transplant 11 can then be tightened to a proper tension by taking the anchoring member 1 by the gripping element 10 and drawing the anchoring member 1, which has the loop of transplant 11 in its slot 8, outwards (into the direction of the arrow in FIG. 5) until a proper tension of the transplant 11 is attained. It may be necessary to bend femur and tibia in relation to each other (this is not seen in FIG. 5) before tightening. When the proper tension is attained, the anchoring member 1 can be secured into the drill-hole, as is shown schematically in FIG. 6.

Figures 6A, 6B:
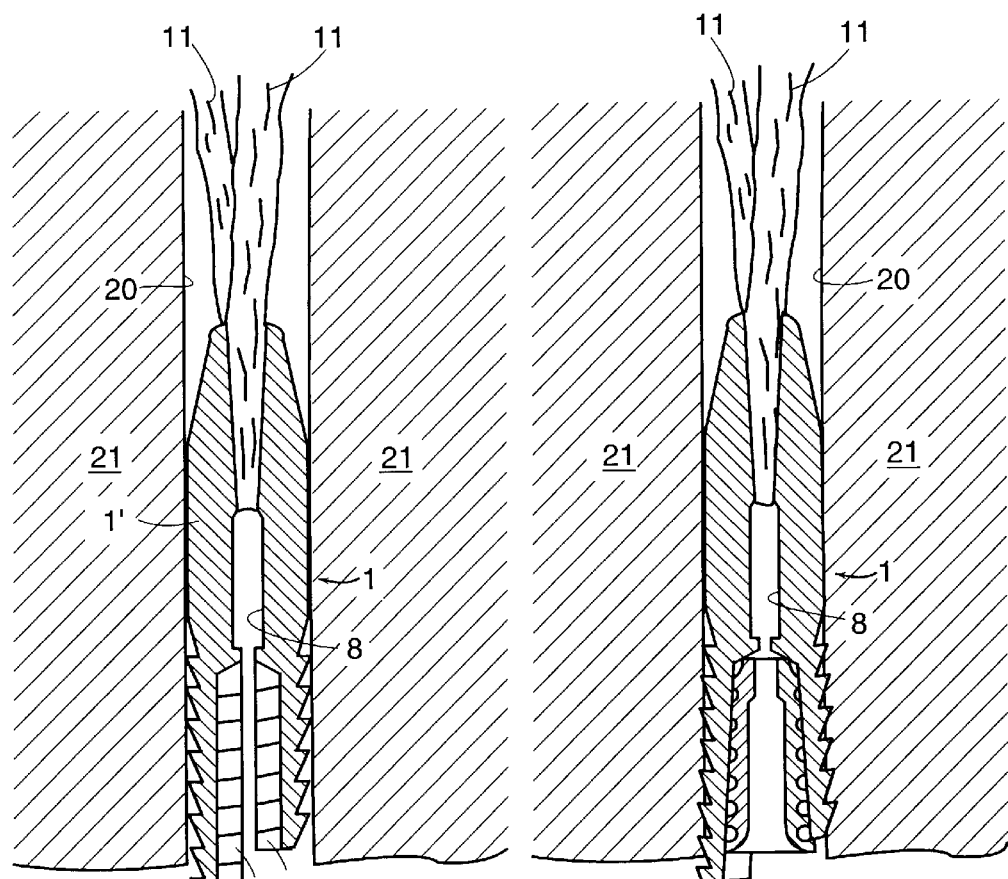
FIG. 6A shows, as a longitudinal cross-sectional figure, how the anchoring member of the invention containing a tendon loop in its slot or opening and having an elongated gripping element has been located inside of a drill-hole in a bone and a clamp member (here a screw) is served with a special tool to lock the anchoring member into the drill-hole in the bone.
FIG. 6B shows, as a longitudinal cross-sectional figure, how the anchoring member of the implant of the invention containing a tendon loop in its slot or opening, has been locked inside of a drill-hole in a bone with the clamp member (here a screw) which has been turned with a special tool between the two arms of the anchoring member to lock the device into the drill-hole in the bone.
Figure 6C:
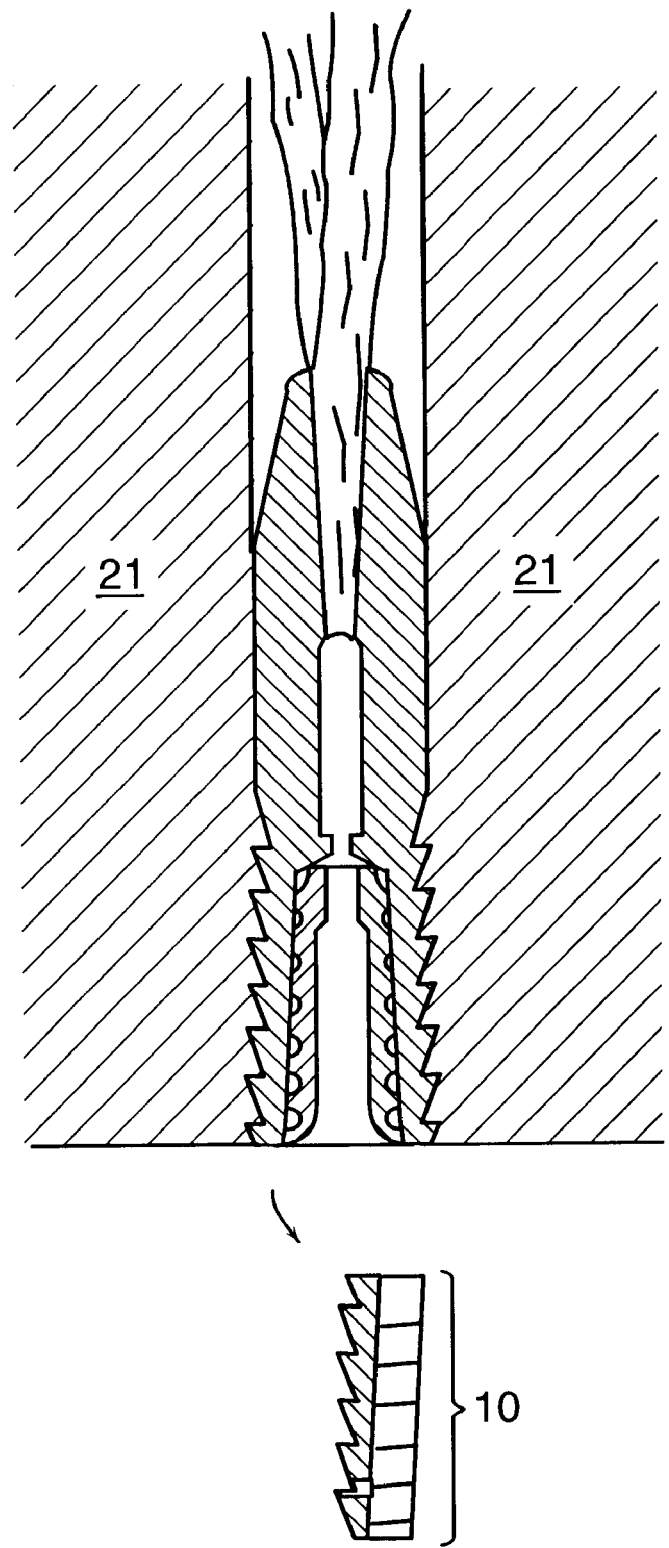
FIG. 6C shows, as a longitudinal cross-sectional figure, how the anchoring member of the implant of the FIG. 6B containing a tendon loop in its slot or opening has been locked inside of a drill-hole in a bone with the clamp member. The anchoring member is substantially co-extensive with the surface of the bone at the opening after the gripping element is removed.

FIG. 6A shows as a schematic cross-sectional figure an anchoring member 1 that has one transplant 11 as a loop in the slot 8. The other end(s) of the looped transplant 11 has/have been drawn through the drill-hole in the tibia into the drill-hole in the femur e.g., with the method described in FIG. 5. Further the transplant has been fixed into the drill-hole in femur e.g., with an interference screw, as was described in FIG. 5. When drawing the transplant loop 11 through the drill-hole 20, the anchor element 1' has also been drawn into the drill-hole 20 in the bone 21 (like tibia). After fixing the other ends of the looped transplant 11 e.g., with an interference screw into the drill-hole in the femur, the transplant loop 11 can be tightened by taking the anchoring member 1 by the gripping element 10 and by pulling the anchoring member 1 outwards from the drill-hole, as was described above and in FIG. 5. The pulling direction is given in FIG. 6A with an open arrow pointing away from the surface of the bone. When the proper tension is attained, the anchoring member 1 can be secured to its position with the clamp member 22 (a screw in FIG. 6A) which is driven (turn) with a special tool 23 between the two arms 2 and 3 of the anchoring member 1, so that the distance between the two arms 2 and 3 of the anchoring member 1 increases and the arms 2 and 3 are locked with frictional forces against the walls of the drill-hole 20 when the locking protrusions on the outer surface of the arms 2 and 3 press against the walls of the drill-hole 20. The two arms 2 and 3 can have protuberances 9 (like spiral-like ridges) on their inner surface for locking of the clamp member 22 between the two arms 2 and 3. As can be seen in FIG. 6B, clamp member 22 is fully engaged between the arms 2 and 3. When the maximum diameter of the clamp member 22 is bigger than the distance between the arms 2 and 3, the clamp member 22 forces the surfaces of arms 2 and 3 (with locking protrusions on their outer surfaces) tightly against the wall of drill-hole 20 so that tight frictional gripping is achieved between the implant and the surrounding bone 21. Thereafter the gripping clement 10 can be cut flush with the bone 21 surface as can be seen from FIG. 6C. Although the clamp member is depicted in FIGS. 6A–C as a screw-type device, it is self-evident that the clamp member can have also other geometries than the screw. The clamp member can be e.g., a cylinder, a cone, a wedge or the like.

Figure 7:
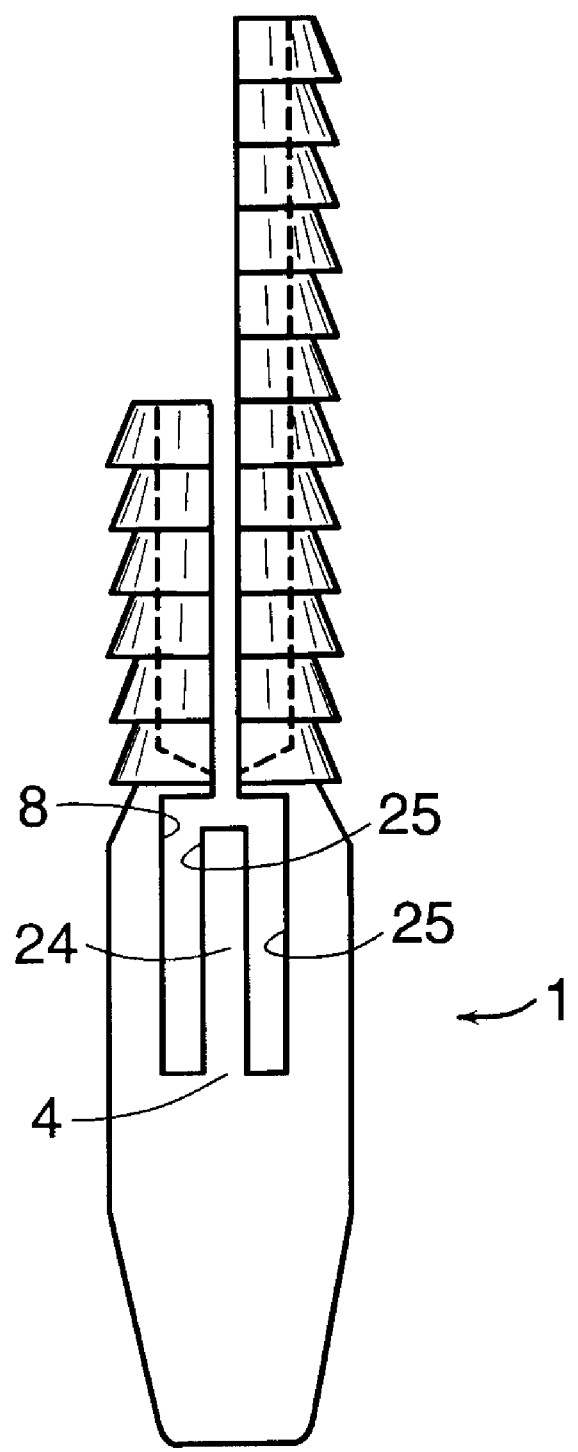
FIG. 7 shows the anchoring member of another embodiment of the invention in which a longitudinal extension into the slot or opening divides the slot into two compartments which serve to separate individual strands of looped tendon grafts.

FIG. 7 shows an optional version for the tendon slot 8 in the anchoring member 1, in which a longitudinal ridge 24 extending from the connection portion 4 into the slot divides the slot into two compartments 25. According to this embodiment of the invention, the tendon is looped around the longitudinal ridge 24 and is coextensive with a portion of the anchor element and on the same side of the anchor element. Alternatively, a separate tendon may be looped through each of the two compartments 25 and then looped around the anchor element away from the locking element. In this manner, each of the two tendons is coextensive with a portion of the anchor element and on opposite sides of the anchor element.

Figure 8A:
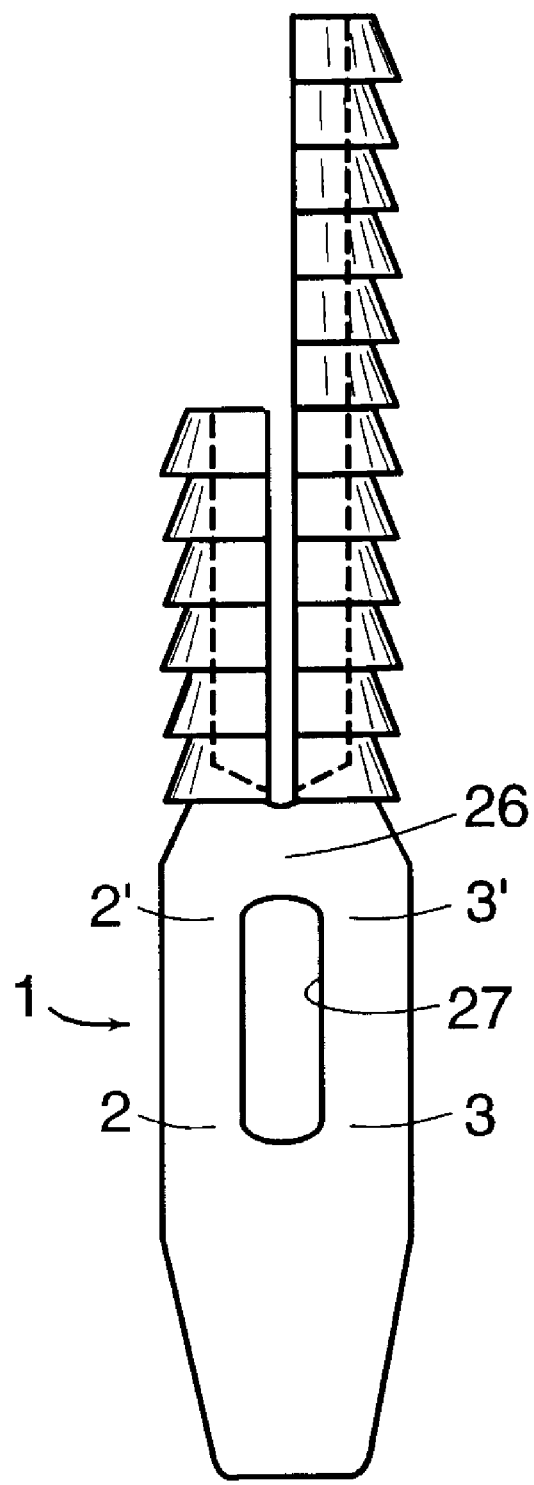
FIG. 8A shows, as side view, an anchoring member, where the first ends of the arms are joined together to form/create a separate hole for the transplant to loop around.

FIG. 8A shows, as side view, an anchoring member 1 where the two arms 2 and 3 fuse at first ends 2' and 3' forming a second connection portion 26 and a separate hole 27 for the tendon to loop around. As with the embodiment shown in FIGS. 3A–B, the tendon is simply inserted into and out of the opening 27 and then looped around the anchor element away from the locking element. In this manner, the tendon is coextensive with a portion of the anchor element and on opposite sides of the anchor element.

Figure 8B:
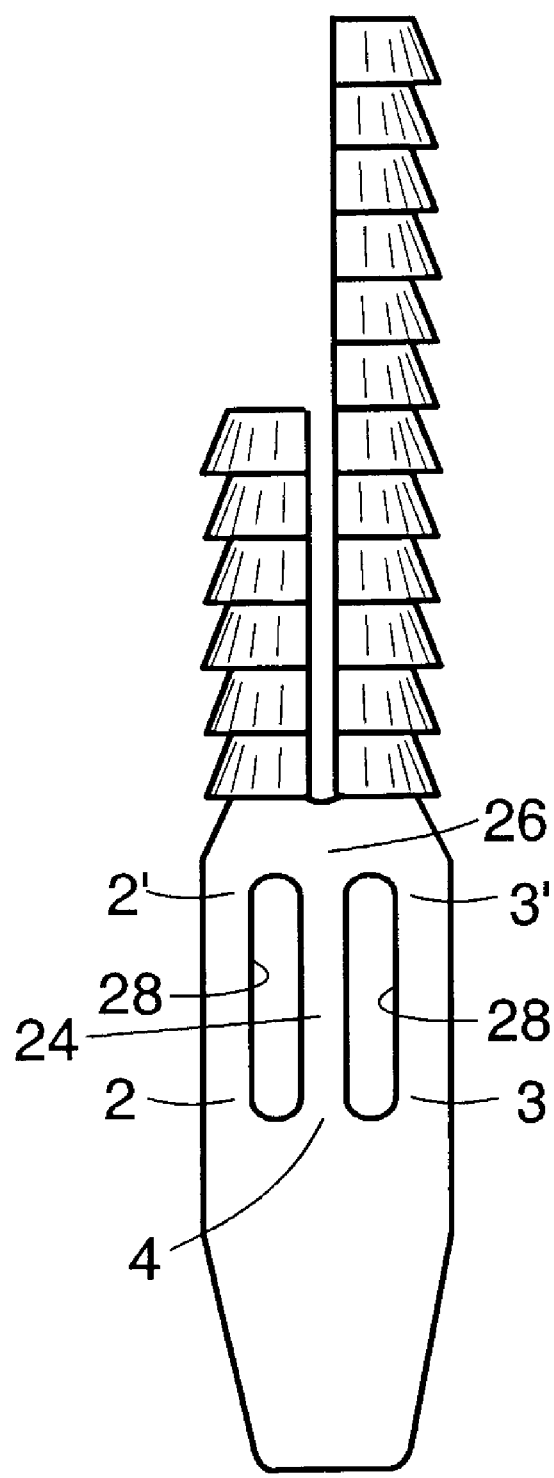
FIG. 8B shows, as side view, an anchoring member where the two transverse connection portions of the first ends of the two arms are connected together with a longitudinal ridge running parallel to the two arms, thus forming two separate holes for the two ligaments to loop around.

FIG. 8B shows, as side view, an optional version for the two transplants to loop around, in which a longitudinal ridge 24 extending from the connection portion 4 fuses with the connection part 26 located between the first ends 2' and 3' of the two arms of the anchor member 2 and 3, thus creating two separate holes 28 for the transplants, in this case tendons, to loop around. According to this embodiment of the invention, the tendon is looped around the longitudinal ridge 24 and is coextensive with a portion of the anchor element and on the same side of the anchor element. Alternatively, a separate tendon may be looped through each of the two holes 28 and then looped around the anchor element away from the locking element. In this manner, each of the two tendons is coextensive with a portion of the anchor element and on opposite sides of the anchor element.

Figures 9A, 9B:
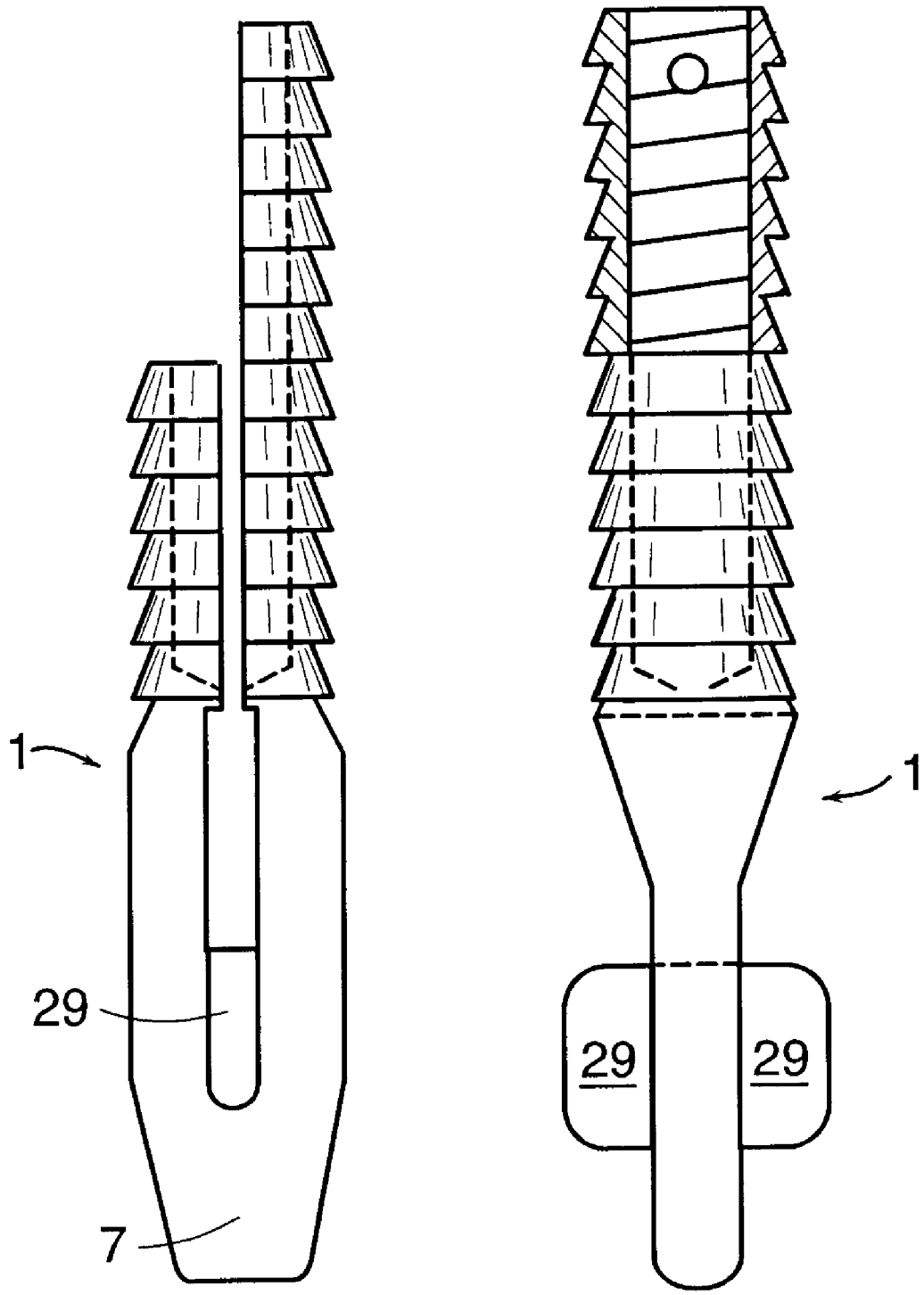
FIG. 9A shows, as side view, the anchoring member of another embodiment of the invention including longitudinal ridges or perpendicular extension tabs on both sides of the anchor element.
FIG. 9B shows the anchoring member of FIG. 9A rotated 90° about its longitudinal axis to more fully show the longitudinal ridges or perpendicular extension tabs on both sides of the anchor element.

FIGS. 9A–B show an optional design for the separation of the two looped tendons. FIG. 9A shows, as side view, an anchoring member 1, in which the flat extension part 7 illustrated in FIGS. 1–3 has two longitudinal ridges 29 extending perpendicularly from respective sides of the anchor element. The longitudinal ridges serve to guide the tendon to one side or the other side of the longitudinal ridges as desired. FIG. 9B is a side view of the anchoring member 1 of FIG. 9A which has been turned 90 degrees clockwise around its long axis. In addition to the designs presented above, other geometries of the anchor element, like an expandable version, are possible in implants of the invention.

Figure 10:
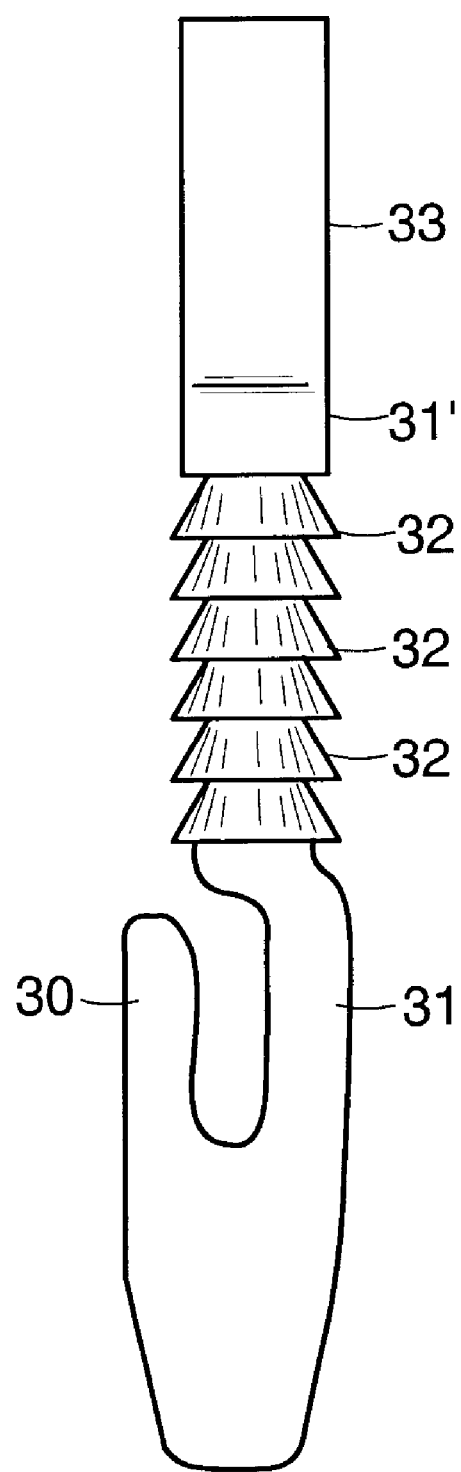
FIG. 10 shows the anchoring member of another embodiment of the invention having a hook design around which a graft can be looped and having locking protrusions on its outer surface and with a gripping element at the end of the locking element.

FIG. 10 shows, as a side view, an anchor member 1 which has one short arm 30 without locking protrusions and one long arm 31 with locking protrusions 32 on its outer surface as also an elongated gripping element 33 emerging from its first end 31'. This type of anchoring member can be locked into a drill-hole in a bone with a clamp member that will be turned or pushed tightly into the dill-hole between the long arm 31 and the wall of the drill-hole. According to this embodiment of the invention, the arms 30 and 31 form a hook structure around which the tendon is looped and drawn away from the locking element. In this manner, the tendon is coextensive with a portion of the anchor element and on opposite sides of the anchor element.

Figure 11:
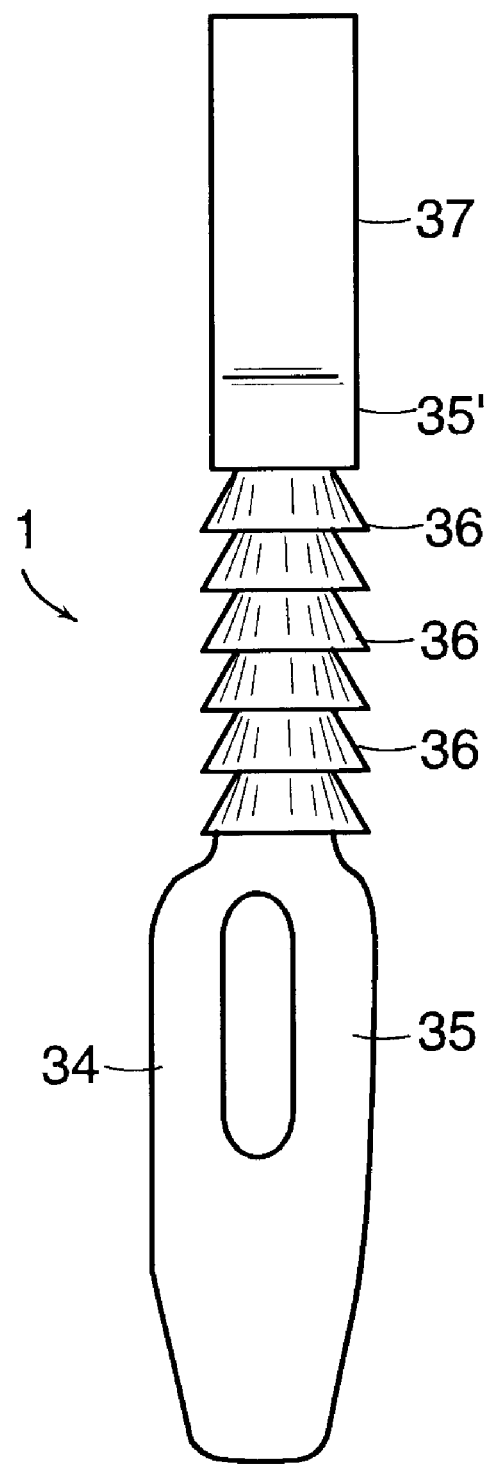
FIG. 11 shows, as a side view, the anchoring member of FIG. 10 where the hook has been closed to form an opening in the anchor element and having locking protrusions on its outer surface and a gripping element.

FIG. 11 shows, as side view, an anchoring member 1, where one arm 34 is joined (fused) with the other arm 35 to form an opening. The anchoring member also has locking protrusions 36 on its outer surface as well as an elongated gripping element 37 emerging from its first end 35'. Also this type of anchoring member can be locked into a drill-hole in a bone with a clamp member that will be turned or pushed tightly into the drill-hole between the long arm 35 and the wall of drill-hole. As with the embodiment of FIG. 8A, the tendon is simply inserted into and out of the opening and then looped around the anchor element away from the locking element. In this manner, the tendon is coextensive with a portion of the anchor element and on opposite sides of the anchor element.

Figure 12A:
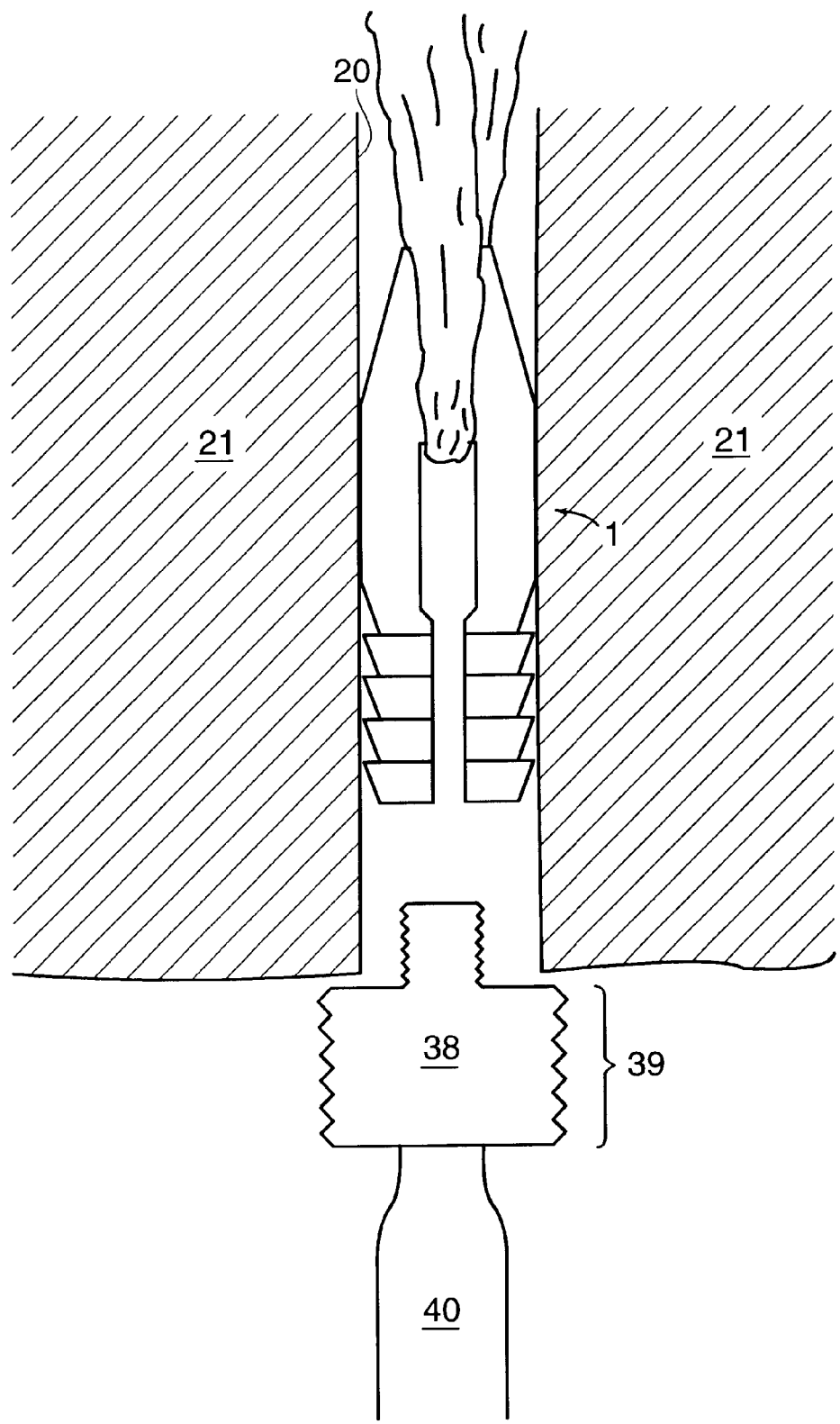
FIG. 12A shows, as a longitudinal cross-sectional figure, how the anchoring member of the invention has been located inside of a drill-hole in a bone and a clamp member (here a screw), a part of which has a diameter substantially larger the diameter of the anchoring member or drill-hole, is served or inserted with a special tool to secure the anchoring member into the drill-hole in the bone.

FIG. 12A shows, as a longitudinal cross-sectional figure how the anchoring member 1, has been located inside of a drill-hole 20 in a bone 21 and a clamp member 38 with an extension 39 the diameter of which is substantially larger than the diameter of the anchoring member or the diameter of the drill-hole, is served with a special tool 40 to secure the anchoring member into the drill-hole in the bone. According to a certain embodiment of the invention, a clamp member 38 which is larger in diameter than that of the drill-hole can still be inserted into the drill-hole without having to trim the opening of the drill-hole as the bone generally will flex to accommodate the clamp member. Alternatively, the clamp member can be made from flexible or compressible material to accommodate insertion into the drill-hole.

Figure 12B:
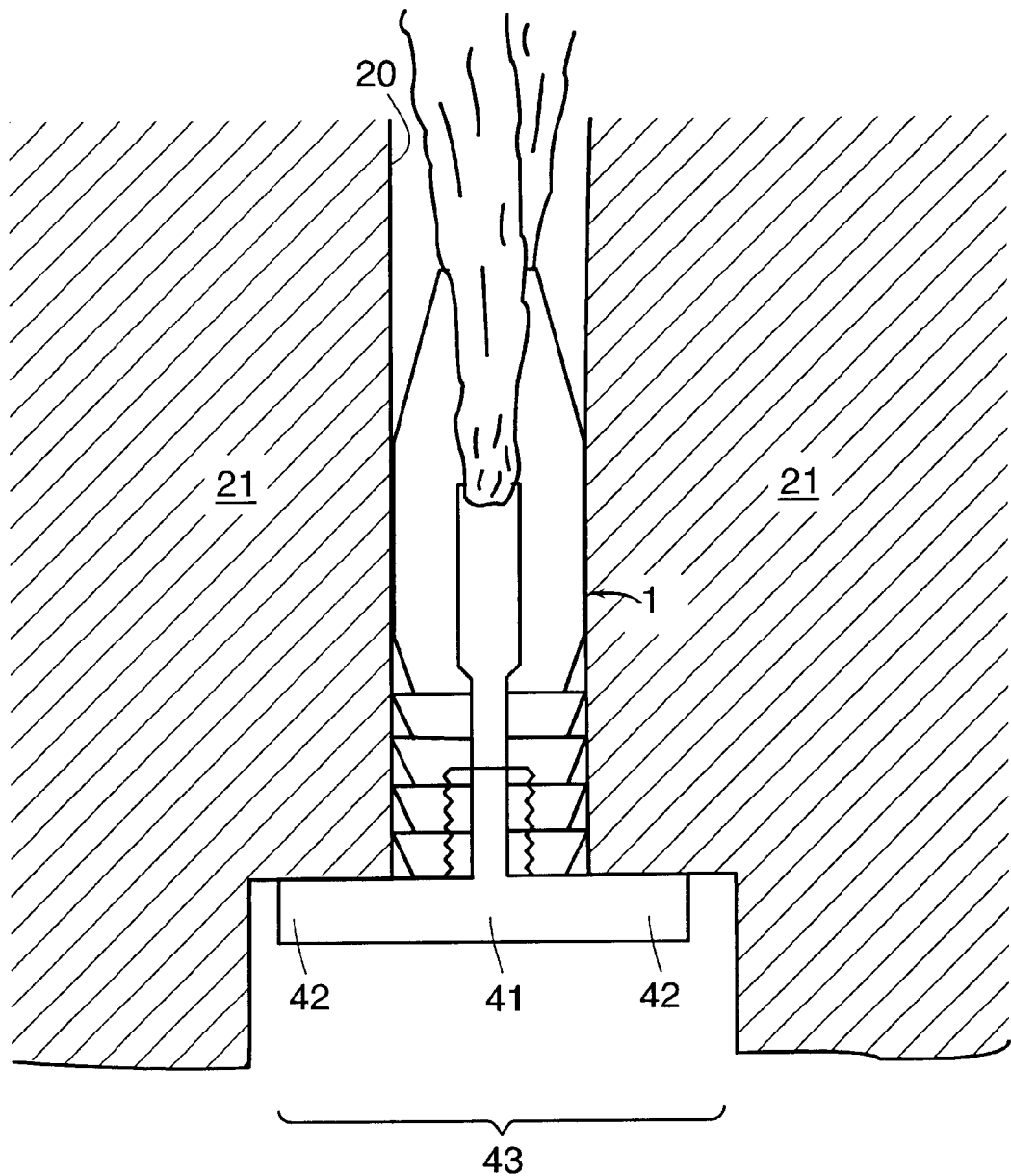
FIG. 12B shows, as a longitudinal cross-sectional figure, how the anchoring member of the implant of the invention has been locked with the clamp member (here a screw) into a drill-hole in a bone, the clamp member having a special recess in its body that fits to the shape of the specially trimmed bone drill-hole.

FIG. 12B shows, as a longitudinal cross-sectional figure, how the anchoring member 1, has been locked into a drill-hole in a bone 21 with the clamp member 41, which has a special recess 42 in its body that fits to the shape of the specially trimmed bone drill-hole 43. Prior to insertion of the clamp member 41, the opening of the drill-hole is trimmed to accommodate the recess 42.

In accordance with certain embodiments, FIGS. 13A–13C illustrate the anchoring member 1 of another embodiment of the invention. Referring to FIG. 13A, an anchoring member 1 is provided with a groove or cut on its surface creating a flap or tab 47. Referring to FIG. 13B, a clamp member 49, depicted as a screw to engage corresponding threads on the inner surface of the locking element, can be inserted to lock the anchoring member into the drill-hole in the bone. Referring to FIG. 13C. as the clamp member is forced into the locking element, the flaps 47 are forced to an outward position to generate additional force between the anchoring member and the wall of the drill-hole.

Figure 14B:
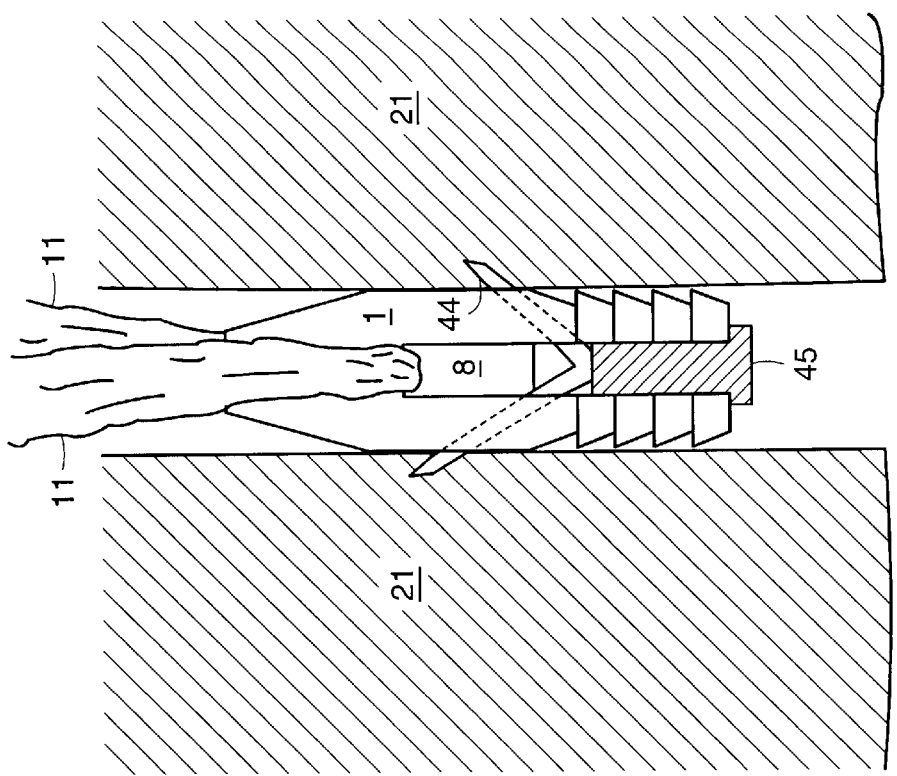
FIG. 14B shows how the anchoring member comprising a tendon loop in its slot has been locked with the two-part clamp member into a drill-hole in a bone, the clamp member being both interlocked with the anchoring member and securely fixing the anchoring member into the drill-hole in the bone.
Figure 14A:
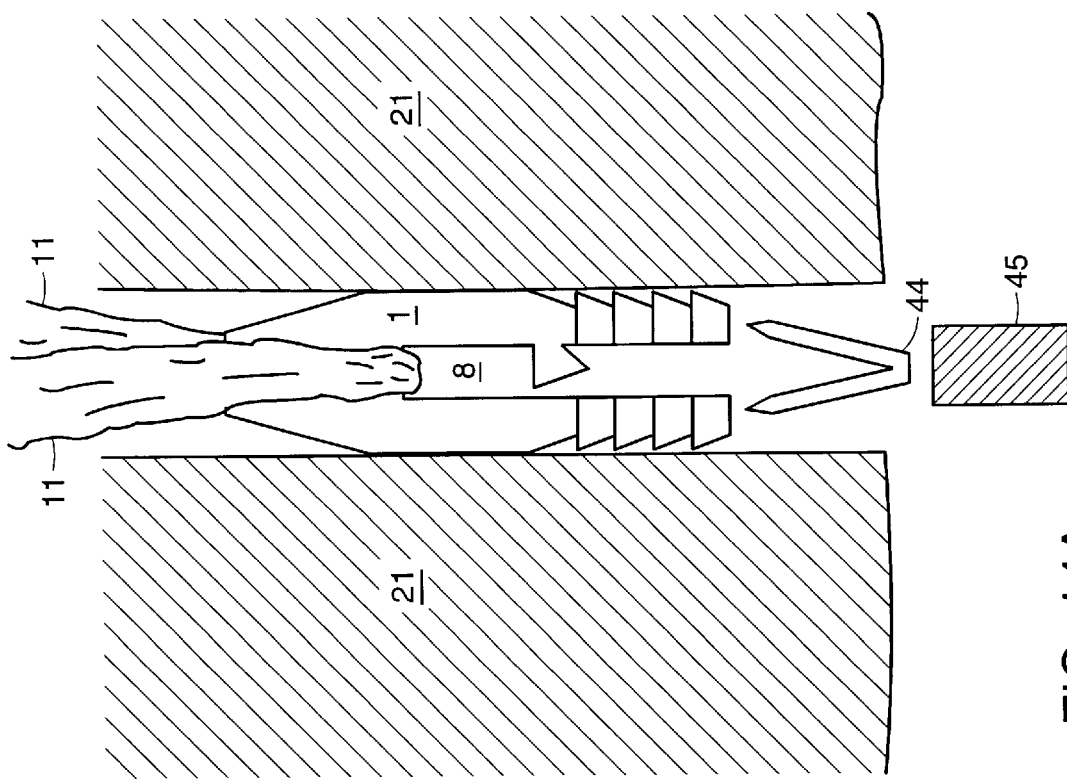
FIG. 14A shows how the anchoring member comprising a tendon loop in its slot is located inside of a drill-hole in a bone and a clamp member consisting of two separate parts being inserted into the drill-hole to couple with the anchoring member.

In accordance with certain embodiments, FIG. 14A depicts an alternate anchoring member and clamp member design. Anchoring member 1 containing a tendon loop 11 in its slot 8 is located inside a drill-hole in a bone 21. A clamp member is provided as a V-shaped insertion part 44 and a stay part 45. The V-shaped insertion part includes pointed tips for penetration into the wall of the drill-hole. The anchoring member includes a V-shaped extension tab for matingly engaging the V-shaped-insertion part. Referring to FIG. 14B, the anchoring member containing a tendon loop 11 in its slot 8 has been locked with the two-part clamp member 44 and 45 into a drill-hole on a bone 21. The V-shaped insertion member has been inserted through the anchor member via openings (not shown) in the arms of the locking element, and further inserted into the wall of the drill-hole. The V-shaped insertion member 44 matingly engages the V-shaped extension tab. The stay member is then inserted into the locking element to retain the V-shaped insertion member in place. It is to be understood that locking elements, insertion members, stay members and clamp members can have any suitable shape or design sufficient to secure the anchoring member within a drill-hole. Other suitable shapes and designs will become readily apparent to those of skill in the art based upon the disclosure herein.

Figure 15A:
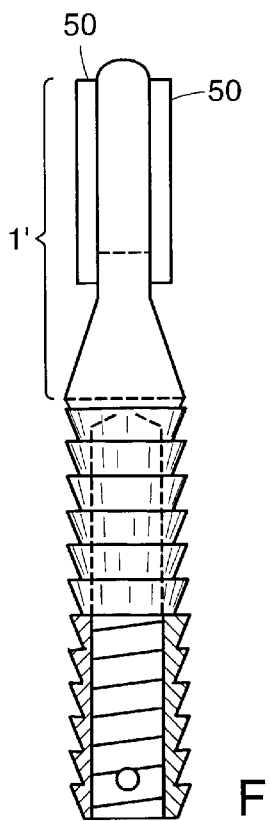
FIG. 15A shows, as side view, an optional design for the anchor element of the anchoring member of the present invention including channels through which tendons may pass.
Figure 15C:
FIG. 15C is a top view of the anchor element of FIG. 15B.
Figure 15B:
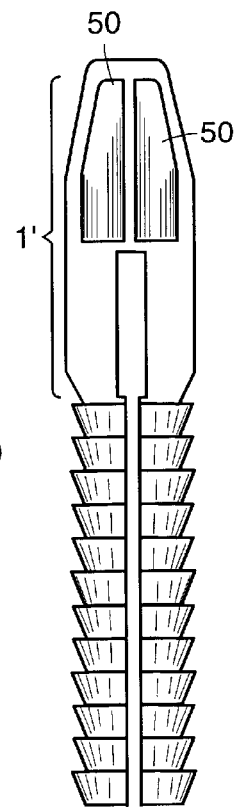
FIG. 15B shows the anchoring member of FIG. 15A rotated 90° about its longitudinal axis to more fully show the channels on both sides of the anchor element.
Figure 15D:
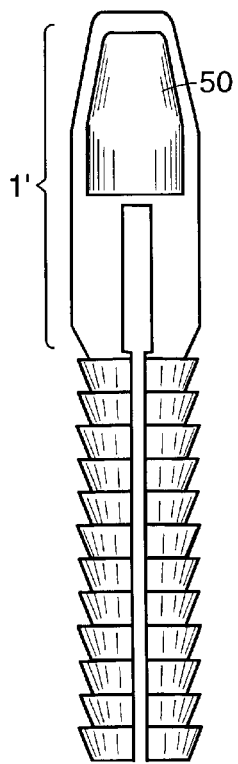
FIG. 15D shows an anchoring member with another design for the anchor element having only one channel on both sides of the anchor element.
Figure 15E:
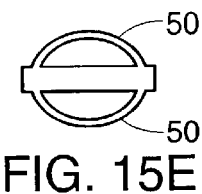
FIG. 15E is a top view of the anchor element of FIG. 15D.
Figure 15F:
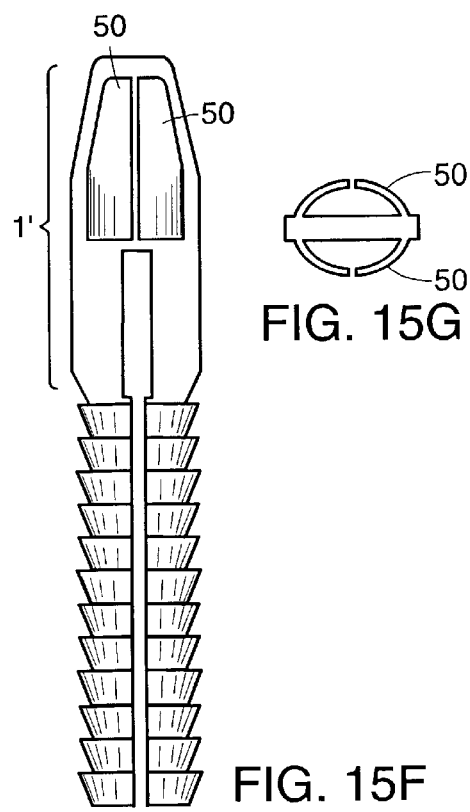
FIG. 15F shows an anchoring member with yet another design for the anchor element including one channel on both sides of the anchor element with the channel being cut longitudinally in half.
Figure 15G:
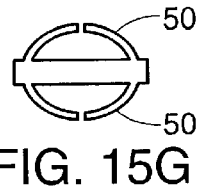
FIG. 15G is a top view of the anchor element of FIG. 15F.
Figure 15H:
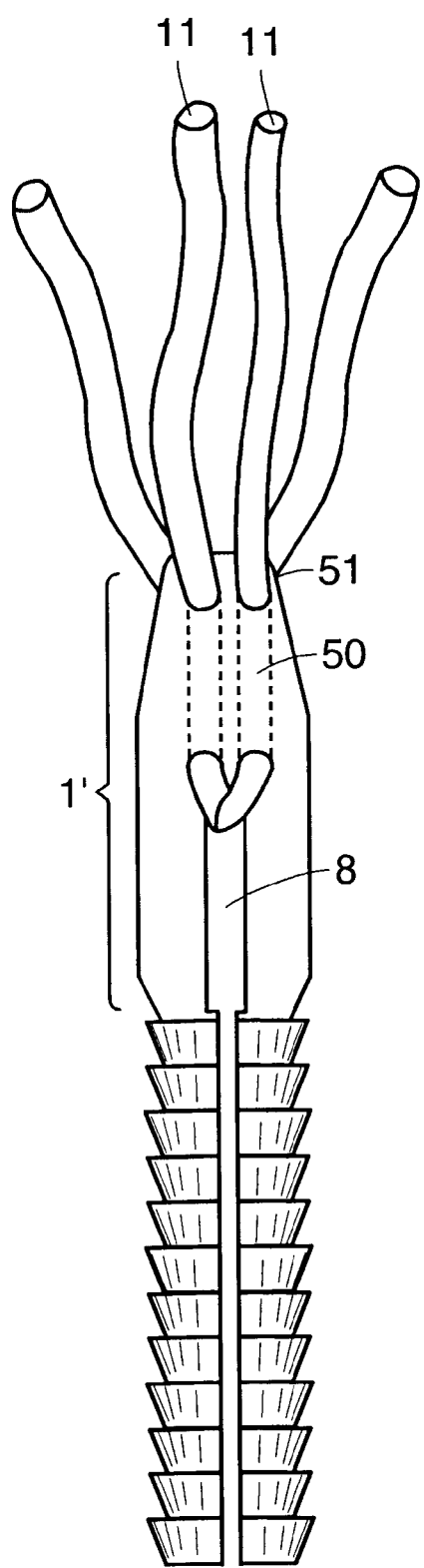
FIG. 15H shows, as a side view, how a two strand tendon graft can be slid into the channels of the anchor element.

An alternate embodiment of the present invention can be seen in FIGS. 15A–H. With reference to FIGS. A–C, anchor element 1' includes two channels 50 disposed on each side of anchor element 1'. The channels 50 are substantially coextensive with anchor element 1'. As can be seen in FIGS. 15C–D, anchor element 1' includes a single channel 50 disposed on each side of anchor element 1'. As can be seen in FIGS. 15F–G the channels can be further modified by cutting the channels 50 in half along the length of the channels. According to this embodiment, the tendon may be threaded through the channel or simply pressed longitudinally into the channel. FIG. 15H depicts the threading of a tendon 11 into the channels 50. According to this aspect of the present invention, a tendon 11 is inserted into a channel 50 on one side of the anchor element beginning at the end of the anchor element 51. The tendon 11 is threaded through the channel and then through the groove, opening or slot 8 in the anchoring member and then into and out of a corresponding channel on the opposite face of the anchor element. A second tendon may be threaded through corresponding channels on opposite faces of the anchor element.

Fixation implants in accordance with the invention can be manufactured of any biocompatible material, e.g., permanent (metal, plastics) or bioabsorbable (biodegradable or resorbable) polymers, copolymers, polymer alloys or composites, e.g., of poly-α-hydroxy acids and other aliphatic biodegradable polyanhydrides, polyorthoesters, polyarganophosphatenes and other bioabsorbable polymers disclosed in numerous publications, e.g., Vainionpää et al. 1989, Weiler et al. 2000, FI 952884, FI-955547 and WO-90/04982 as well as in the reference publications mentioned in the aforementioned publications.

For example, implants in accordance with the invention can be manufactured of biodegradable polymers by using one polymer or polymer alloy. The implants can also be reinforced by reinforcing the material by fibers manufactured of resorbable polymer or polymer alloy, or of biodegradable glass, such as tri-calcium phosphate, bioactive glass or CaM (c.f. e.g., EP 146398). Ceramic and glass (like bioactive glass) powders can also be used as additives (fillers) in implants to promote new bone formation.

Implants according to the invention can also contain layered parts comprising e.g., (a) a flexible layer, a surface layer improving the toughness and/or ability of the implant to act as the hydrolysis barrier and (b) a stiff inner layer.

Surgical implants in accordance with the invention can be manufactured of biodegradable polymers, which may or not contain suitable biodegradable reinforcement fibers and/or particle fillers by means of various methods used in plastic technology, such as injection molding, extrusion and fibrillation and molding related thereto (e.g., publication U.S. Pat. No. 4,968,317) or by means of compression molding, wherein the pieces are shaped of the raw material by employing heat and/or compression. Also mechanical machining (e.g., cutting, drilling, lathing, grinding etc.) can be used.

According to an advantageous embodiment the implant comprises holes or open porosity to facilitate tissue (like bone) growth, inside of the implant. Such holes or pores typically have a diameter from 100 $\mu$m to 2000 $\mu$m. The holes or pores may be filled at least partially with cancellous bone of the patient and/or with ceramic or glass bone substitute powder or granules (like with bioactive glass) to accelerate their filling with new bone. Such new bone inside of holes or pores of the implant facilitates the final healing and ossification of the drill-hole when the implant biodegrades and disappears from the drill-hole.

It is possible to manufacture implants of the invention of aforementioned raw materials also by using so-called dissolving techniques, in which at least part of the polymer is dissolved into a suitable solvent or softened by means of a solvent and the material or the material alloy is compressed into a piece by means of pressure and possibly by means of slight heat, wherein the dissolved or softened polymer glues the material into a macroscopic piece wherefrom the solvent is removed by evaporation.

It is natural that the implants of the invention can also contain various additives for facilitating the processability of the material (e.g., stabilizers, antioxidants or plasticizers) or for changing its properties (e.g., plasticizers or ceramic powder materials or biostable fibers, such as carbon fibres) or for facilitating its treatment (e.g., colorants).

According to one advantageous embodiment the implant of the invention can contain some bioactive agent or agents, such as antibiotics, chemotherapeutic, agents, agents activating healing of wounds, growth factor(s), bone morphogenic protein(s), anticoagulant (such as heparin) etc. Such bioactive implants are particularly advantageous in clinical use, because they have, in addition to their mechanical effect, also biochemical, medical and other effects to facilitate tissue healing and/or regeneration.

The functionality of the invention is illustrated in the following example:

EXAMPLE 1

The aim of this example is to illustrate the fixation strength provided by the fixation implant of this invention and to compare it with that provided by prior art implants (a conventional titanium interference screw: SoftSilk, Smith & Nephew Inc., Andover, Mass. U.S.A. diameter 8.0 mm, length 25 mm and two (tandem) Spiked washers: Linvatec, Largo, Fla., U.S.A. 17 mm×1.3 mm) in an anterior cruciate ligament (ACL) reconstruction using a human four-strand semitendinosus-and-gracilis-tendon (ST/G) graft in the porcine knee specimen.

Implants as depicted in FIG. 1 were manufactured with length of 40 mm and a diameter of 10 mm. The four-strand ST/G-fixation implant construct was assembled as illustrated in FIGS. 3A–C, after which the length-adjusted free tendon ends of both the semitendinosus and gracilis tendon were sutured for 30 mm with a 2-0 suture using a running baseball stitch (whip stitch). The graft-implant construct was inserted into a drill-hole of 10 mm in diameter, which was made through the tibial metaphysis using a cannulated drill bit. The implant was finally secured by inserting a screw (diameter 7.0 mm, length 15 mm) into the dilation hole of the implant as illustrated in FIGS. 5A–C. In case of the prior art implants, the four-strand ST/G-graft was assembled according to standard procedures; that is, by suturing both ends of the doubled semitendinosus-and gracilis-tendons, after which the graft was pulled into the tibial drill-hole made using appropriately sized router(s). For the interference screw, a 2.0 mm screw guide wire was inserted between the graft and the posterior aspect of the distal tunnel and the interference screw was advanced fully until the head was barely below the chondral surface of the tibial plateau. For the tandem Spiked Washers, the sutured end of the ST/G-graft was placed under the washers each of which was then fixed on the anteromedial cortex of the tibia with a cortical screw (diameter 4.5 mm, length 60 mm).

For the biomechanical testing, the sutured free end of the ST/G-grafts of all constructs was fixed into the upper (moving) jaw of a tensile testing machine (Lloyd LRSK, available from J J Lloyd Instruments, Southampton, UK) and the tibia was secured into the lower jaw, and the construct was subjected to a vertical tensile loading parallel with the drill-hole at a strain rate of 50 m/min until failure. Five samples were tested in each group. Table 1 gives the measured linear ($F_{yield}$) and ultimate ($F_{max}$) forces for each of the three testes implants.

TABLE 1*

|  | $F_{yield}$ | $F_{max}$ |
|---|---|---|
| Titanium interference screw (n = 5) | 493 N (344–617) | 588 N (352–775) |
| Tandem Spiked Washers (n = 5) | 748 N (572–927) | 834 N (605–1090) |
| Present invention (n = 5) | 934 N (776–1065) | 978 N (925–1128) |

*The values represent mean (range).

The results of this test indicate that the implant of the present invention provides a clearly stronger and more appropriate fixation of the ST/G-graft than the prior art implants. In addition, both the assembly and fixation of the ST/G-graft were clearly less time consuming and laborious while using the present invention than the other implants tested.

While preferred embodiments of the endosteal graft fixation anchor have been shown and described herein, the present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes that fall within the meaning and range of equivalency of the claims are to be embraced within their scope.

What is claimed is:

1. An endosteal anchor for fixation of a transplant into a drill-hole in a bone, the anchor comprising:
an anchoring member and a clamp member, wherein the anchoring member comprises an anchor element with at least one opening suitable for the transplant to loop around and at least one locking element for fixing the anchoring member within the drill-hole, the anchor element and locking element being coupled in series in relation to each other, and the clamp member being engageably disposable in relation to the locking element for fixing the anchoring member into the drill-hole.

2. The anchor of claim 1, wherein the thickness of the surface of the anchor element around which the transplant loops is substantially smaller than the diameter of the drill-hole into which the anchor is secured.

3. The anchor of claim 1 wherein the anchoring member and the clamp member each comprise a plurality of interlocking members.

4. The anchor of claim 2 wherein the anchoring member and the clamp member each comprise a plurality of interlocking members.

5. The anchor of claim 3 wherein the interlocking members provide means for interlocking the anchoring member and the clamp member together and locking the anchor within the drill-hole.

6. The anchor of claim 1 wherein the locking element comprises two substantially parallel arms and wherein the distance between the two arms of the anchoring member are capable of increasing and the arms are locked with frictional forces against the walls of the drill-hole when the arm(s) press against the walls of the drill-hole.

7. The anchor of claim 1 wherein the anchor element comprises an extension part that urges the transplant against a bone surface within the drill-hole.

8. The anchor of claim 7 wherein the extension part comprises a substantially flat shape.

9. The anchor of claim 7 wherein the extension part comprises one or more longitudinal or horizontal ridges on its surface.

10. The anchor of claim 7 wherein the extension part is expandable.

11. The anchor of claim 6 wherein first ends of the two arms are joined.

12. The anchor of claim 1 wherein the at least one opening includes a longitudinal ridge to create two slots for the transplant(s) to pass around.

13. The anchor of claim 1 wherein the at least one opening includes a longitudinal ridge to create two separate holes for the transplant(s) to pass around.

14. The anchor of claim 1 wherein the locking element further includes an elongated gripping element.

15. The anchor of claim 1 wherein the anchoring member comprises a recess for the insertion of a gripping instrument.

16. An anchor system for fixation of an artificial or natural ligament or tendon into a drill-hole in a bone, the system comprising of at least an anchoring member and a clamp member, wherein the anchoring member comprises of:

a U-shaped anchor element for placement into a drill-hole in the bone, from the anchor element emerging two arms with first ends, and second ends, which join at a connecting portion to create a slot, around which the ligament passes;

and a clamp member that will be adjustably, and at least partly, mounted between the two arms of the anchoring member or between one arm of the anchoring member and a wall of the drill-hole to lock the anchor into the drill-hole.

17. The anchor of claim 16 wherein the anchoring member comprises locking protrusions.

18. The anchor of claim 16 wherein at least part of the clamp member has a diameter substantially greater than a diameter of the anchoring member or the drill-hole.

19. The anchor of claim 16 wherein a distance between two arms of the anchoring member increases and the arms are locked with frictional forces against the walls of the drill-hole when the arms press against the walls of the drill-hole.

20. The anchor of claim 16 wherein the anchor element comprises an extension part that urges the transplant against a bone surface within the drill-hole.

21. The anchor of claim 20 wherein the extension part comprises a substantially flat shape.

22. The anchor of claim 20 wherein the extension part comprises longitudinal or horizontal ridges on its surface.

23. The anchor of claim 20 wherein the extension part is expandable.

24. The anchor of claim 16 wherein the first ends of the two arms are joined.

25. The anchor of claim 16 wherein a longitudinal ridge extends within the slot to create two slots for the transplant(s) to pass around.

26. The anchor of claim 16 wherein a longitudinal ridge extends within the slot to create two separate holes for the transplant(s) to pass around.

27. The anchor of claim 16 wherein at least one first end of the two arms includes an elongated gripping element.

28. The anchor of claim 16 wherein the anchoring member has a recess for the insertion of a gripping instrument.

29. An anchoring member for fixation of a graft ligament or tendon into a drill-hole in a bone comprising:

an anchor element configured to retain the graft, and a locking element extending from the anchor element and configured to frictionally engage a wall of the drill-hole.

30. The anchoring member according to claim 29 wherein the locking element comprises locking protrusions.

31. The anchoring member according to claim 29 further comprising a clamp member for engaging the locking element.

32. The anchoring member according to claim 29 wherein the anchor element and the locking element are connected in series relation and with the anchor element configured to urge the graft against the wall of the drill-hole.

33. The anchoring member according to claim 29 wherein the locking element comprises two arms extending from the anchor element and configured to frictionally engage a wall of the drill-hole.

34. The anchoring member according to claim 32 wherein the anchor element is substantially flat in shape.

35. The anchoring member according to claim 32 wherein the anchor element comprises one or more longitudinal or horizontal ridges on its surface.

36. The anchoring member according to claim 32 wherein the anchor element is expandable.

37. The anchoring member according to claim 29 wherein the anchor element includes a slot into which the graft is looped.

38. The anchoring member according to claim 29 wherein the anchor element includes two slots into which the graft is looped.

39. The anchoring member according to claim 29 wherein the anchor element includes two separate holes into which the graft is looped.

40. The anchoring member according to claim 29 further including an elongated gripping element.

41. The anchoring member of claim 29 wherein the locking element includes extendable tabs for frictionally engaging a wall of the drill-hole.

42. The anchoring member of claim 41 wherein the extendable tabs are moveably responsive to insertion of a clamp member.

43. The anchoring member of claim 31 wherein the clamp member comprises an insertion part configured to engage the anchoring member and a wall of the drill-hole.

44. The anchoring member of claim 43 further comprising a stay part for securing the insertion part to the anchoring member and the wall of the drill-hole.

45. The anchoring member of claim 29 wherein the anchor element includes one or more channels on each face of the anchor element for receiving the graft.

46. A method for securing a graft within a drill-hole in a bone comprising securing a graft to an anchoring member comprising an anchor element configured to retain the graft and a locking element extending from the anchor element and configured to frictionally engage a wall of the drill-hole;

extending the graft along the anchor element and away from the locking element;

placing the anchoring member entirely within the drill-hole such that the locking element is free of contact with the graft with the graft extending away from the locking element; and securing the anchoring member within the drill-hole.

47. The method of claim 46 wherein the step of securing the anchoring member within the drill-hole includes engaging a clamp member to the locking element.

48. The method of claim 46 wherein the locking element comprises locking protrusions.

49. The method of claim 46 wherein the anchor element and the locking element are connected in series relation and with the anchor element configured to urge the graft against the wall of the drill-hole.

50. The method of claim 46 wherein the locking element comprises two arms extending from the anchor element and configured to frictionally engage a wall of the drill-hole.

51. The method of claim 46 wherein the step of securing the graft includes looping the graft around a slot in the anchor element.

52. The method of claim 46 wherein the step of securing the graft includes looping the graft through an opening in the anchor element.

53. The method of claim 46 wherein the anchoring member includes a gripping element for adjusting the anchoring member within the drill-hole.

54. An anchor for fixation of a transplant into a drill-hole in a bone, the anchor comprising:

an anchoring member and a clamp member, wherein the anchoring member comprises an anchor element with at least one opening suitable for the transplant to loop around and at least one locking element for fixing the anchoring member within the drill-hole, the anchor element and locking element being coupled in series in relation to each other, the anchor element including an extension part that urges the transplant against a bone surface within the drill-hole, the locking element including at least one elongated gripping element, and the clamp member being engageably disposable in relation to the locking element for fixing the anchoring member into the drill-hole.

55. An anchoring member for fixation of a transplant into a drill-hole in a bone comprising:

an anchor element configured to retain the transplant, the anchor element including an extension part that urges the transplant against a bone surface within the drill-hole, and a locking element extending from the anchor element and configured to frictionally engage a wall of the drill hole with the locking element including at least one elongated gripping element.

56. An anchor system for fixation of a transplant into a drill-hole in a bone, the system comprising an anchoring member for placement into a drill-hole in a bone and a clamp member, the anchoring member including a U-shaped anchor element defining a slot around which a transplant passes and having two parallel arms, the anchor element further having an extension part that urges the transplant against a bone surface within the drill-hole, at least one of the two arms further including an elongated gripping element, and a clamp member configured to be adjustably, and at least partly, mounted between the two arms of the anchoring member or between one arm of the anchoring member and a wall of the drill-hole to lock the anchor into the drill-hole.

57. A method for securing a transplant within a drill-hole in a bone comprising engaging a transplant and an anchoring member comprising an anchor element configured to retain the transplant and a locking element extending from the anchor element and configured to frictionally engage a wall of the drill-hole, the locking element including a gripping element for adjusting the anchoring member within the drill-hole;

extending the transplant along the anchor element and away from the locking element;

placing the anchoring member entirely within the drill-hole such that the locking element is free of contact with the transplant and with the transplant extending away from the locking element;

urging the transplant against the wall of the drill-hole;

adjusting the anchoring member within the drill-hole; and securing the anchoring member within the drill-hole.

58. An anchor for fixation of a transplant into a drill-hole in a bone, the anchor comprising:

an anchoring member and a clamp member, wherein the anchoring member comprises an anchor element with at least one opening suitable for the transplant to loop around and at least one locking element for fixing the anchoring member within the drill-hole, the anchor element and locking element being coupled in series in relation to each other, the anchor element including an extension part that urges the transplant against a bone surface within the drill-hole, the locking element including an interior to receive a clamp member, and the clamp member being engageably disposable in relation to the locking element for fixing the anchoring member into the drill-hole.

59. An anchoring member for fixation of a transplant into a drill-hole in a bone comprising:

an anchor element configured to retain the transplant, the anchor element including an extension part that urges the transplant against a bone surface within the drill-hole, and a locking element extending from the anchor element and configured to frictionally engage a wall of the drill hole with the locking element having an interior to receive a clamp member.

60. An anchor system for fixation of a transplant into a drill-hole in a bone, the system comprising an anchoring member for placement into a drill-hole in a bone and a clamp member, the anchoring member including a U-shaped anchor element defining a slot around which a transplant passes and having two parallel arms forming a locking element, the anchor element further having an extension part that urges the transplant against a bone surface within the drill-hole, the locking element including an interior for receiving a clamp member, and the clamp member configured to be adjustably, and at least partly, mounted between the two arms of the anchoring member or between one arm of the anchoring member and a wall of the drill-hole to lock the anchor into the drill-hole.

61. An endosteal anchor for fixation of a transplant into a drill-hole in a bone, the anchor comprising:

an anchoring member and a clamp member, wherein the anchoring member comprises an anchor element with at least one opening suitable for the transplant to loop around and at least one locking element for fixing the anchoring member within the drill-hole, the anchor element and locking element being coupled in series in relation to each other, and the clamp member being engageably disposable in relation to the locking element for fixing the anchoring member into the drill-hole, wherein the at least one opening includes a longitudinal ridge to create two slots for the transplant(s) to pass around.

62. An endosteal anchor for fixation of a transplant into a drill-hole in a bone, the anchor comprising:

an anchoring member and a clamp member, wherein the anchoring member comprises an anchor element with at least one opening suitable for the transplant to loop around and at least one locking element for fixing the anchoring member within the drill-hole, the anchor element and locking element being coupled in series in relation to each other, and the clamp member being engageably disposable in relation to the locking element for fixing the anchoring member into the drill-hole, wherein the at least one opening includes a longitudinal ridge to create two separate holes for the transplant(s) to pass around.

63. An endosteal anchor for fixation of a transplant into a drill-hole in a bone, the anchor comprising:

an anchoring member and a clamp member, wherein the anchoring member comprises an anchor element with at least one opening suitable for the transplant to loop around and at least one locking element for fixing the anchoring member within the drill-hole, the anchor element and locking element being coupled in series in relation to each other, and the clamp member being engageably disposable in relation to the locking element for fixing the anchoring member into the drill-hole, wherein the locking element further includes an elongated gripping element.

64. An anchoring member for fixation of a graft ligament or tendon into a drill-hole in a bone comprising:

an anchor element configured to retain the graft, and a locking element extending from the anchor element and configured to frictionally engage a wall of the drill-hole;

wherein the anchor element comprises a hook-shaped extension around which the graft is looped.

\* \* \* \* \*